(12) United States Patent
Reiley et al.

(10) Patent No.: US 8,066,740 B2
(45) Date of Patent: *Nov. 29, 2011

(54) FACET JOINT PROSTHESES

(75) Inventors: Mark A. Reiley, Piedmont, CA (US);
Robert M. Scribner, Boulder, CO (US);
Lawrence R. Jones, Conifer, CO (US);
David Stinson, Woodinville, WA (US)

(73) Assignee: GMEDELAWARE 2 LLC, Audubon, PA (US)

(*) Notice: Subject to any disclaimer, the term of this patent is extended or adjusted under 35 U.S.C. 154(b) by 742 days.

This patent is subject to a terminal disclaimer.

(21) Appl. No.: 11/577,872

(22) PCT Filed: Oct. 21, 2005

(86) PCT No.: PCT/US2005/038087
§ 371 (c)(1),
(2), (4) Date: Dec. 7, 2007

(87) PCT Pub. No.: WO2006/047363
PCT Pub. Date: May 4, 2006

(65) Prior Publication Data
US 2008/0200953 A1 Aug. 21, 2008

(51) Int. Cl.
*A61B 17/58* (2006.01)
*A61F 2/44* (2006.01)

(52) U.S. Cl. ....................................... 606/247

(58) Field of Classification Search .......... 606/246–252; 623/17.11–17.16
See application file for complete search history.

(56) References Cited

U.S. PATENT DOCUMENTS

| | | | |
|---|---|---|---|
| 1,308,451 | A | 7/1919 | Schachat |
| 2,502,902 | A | 4/1950 | Tofflemire |
| 2,930,133 | A | 3/1960 | Thompson |
| 2,959,861 | A | 11/1960 | Stromquist |
| 3,596,656 | A | 8/1971 | Kaute |
| 3,710,789 | A | 1/1973 | Ersek |
| 3,726,279 | A | 4/1973 | Barefoot et al. |
| 3,867,728 | A | 2/1975 | Stubstad et al. |
| 3,875,595 | A | 4/1975 | Froning |
| 3,941,127 | A | 3/1976 | Froning |
| 4,040,130 | A | 8/1977 | Laure |

(Continued)

FOREIGN PATENT DOCUMENTS
DE 10135771 A1 7/2001
(Continued)

OTHER PUBLICATIONS

Ochoa et al.; U.S. Appl. No. 12/377,546 entitled "Spinal implant," filed Feb. 13, 2009.

(Continued)

*Primary Examiner* — Pedro Philogene

(57) ABSTRACT

Cephalad and caudal vertebral facet joint prostheses and methods of use are provided. A pair of fixation elements are adapted to be secured within a vertebra in an orientation that best assures a secure and durable attachment to cortical and/or cancellous bone. Artificial facet joint surfaces are mounted on the fixation elements, either directly or with the aid of a support. The artificial facet joint structure may be carried by an arm. The artificial facet joint structure is adapted for articulation with a complementary natural or artificial facet joint structure. Bilateral prostheses may by coupled by a brace to further secure and stabilize the prostheses. Artificial facet joints can be used in combination with artificial intervertebral discs to treat a spinal pathology.

30 Claims, 22 Drawing Sheets

U.S. PATENT DOCUMENTS

| | | | |
|---|---|---|---|
| 4,123,848 A | 11/1978 | Emmerich et al. | |
| 4,156,296 A | 5/1979 | Johnson et al. | |
| 4,210,317 A | 7/1980 | Spann et al. | |
| 4,231,121 A | 11/1980 | Lewis | |
| 4,271,836 A | 6/1981 | Bacal et al. | |
| 4,349,921 A | 9/1982 | Kuntz | |
| 4,394,370 A | 7/1983 | Jefferies | |
| 4,472,840 A | 9/1984 | Jefferies | |
| 4,502,161 A | 3/1985 | Wall | |
| 4,554,914 A | 11/1985 | Kapp et al. | |
| 4,611,581 A | 9/1986 | Steffee | |
| 4,633,722 A | 1/1987 | Beardmore et al. | |
| 4,693,722 A | 9/1987 | Wall | |
| 4,697,582 A | 10/1987 | William | |
| 4,710,075 A | 12/1987 | Davison | |
| 4,759,769 A | 7/1988 | Hedman et al. | |
| 4,772,287 A | 9/1988 | Ray et al. | |
| 4,778,472 A | 10/1988 | Homsy et al. | |
| 4,795,469 A | 1/1989 | Oh | |
| 4,805,602 A | 2/1989 | Puno et al. | |
| 4,863,477 A | 9/1989 | Monson | |
| 4,904,260 A | 2/1990 | Ray et al. | |
| 4,911,718 A | 3/1990 | Lee et al. | |
| 4,917,701 A | 4/1990 | Morgan | |
| 4,932,975 A | 6/1990 | Main et al. | |
| 4,950,270 A | 8/1990 | Bowman et al. | |
| 4,955,916 A | 9/1990 | Carignan et al. | |
| 4,957,495 A | 9/1990 | Kluger | |
| 4,987,904 A | 1/1991 | Wilson | |
| 5,000,165 A | 3/1991 | Watanabe | |
| 5,015,255 A | 5/1991 | Kuslich | |
| 5,019,081 A | 5/1991 | Watanabe | |
| 5,047,055 A | 9/1991 | Bao et al. | |
| 5,062,845 A | 11/1991 | Kuslich et al. | |
| 5,070,623 A | 12/1991 | Barnes | |
| 5,071,437 A | 12/1991 | Steffee | |
| 5,092,866 A | 3/1992 | Breard et al. | |
| 5,098,434 A | 3/1992 | Serbousek | |
| 5,108,399 A | 4/1992 | Eitenmuller et al. | |
| 5,129,900 A | 7/1992 | Asher et al. | |
| 5,147,404 A | 9/1992 | Downey | |
| 5,171,280 A | 12/1992 | Baumgartner | |
| 5,192,326 A | 3/1993 | Bao et al. | |
| 5,258,031 A | 11/1993 | Salib et al. | |
| 5,261,910 A | 11/1993 | Warden et al. | |
| 5,284,655 A | 2/1994 | Bogdansky et al. | |
| 5,300,073 A | 4/1994 | Ray et al. | |
| 5,303,480 A | 4/1994 | Chek | |
| 5,306,308 A | 4/1994 | Gross et al. | |
| 5,306,309 A | 4/1994 | Wagner et al. | |
| 5,312,409 A | 5/1994 | McLaughlin et al. | |
| 5,314,429 A | 5/1994 | Goble | |
| 5,314,476 A | 5/1994 | Prewett et al. | |
| 5,314,486 A | 5/1994 | Zang et al. | |
| 5,314,489 A | 5/1994 | Hoffman et al. | |
| 5,314,492 A | 5/1994 | Hamilton et al. | |
| 5,329,933 A | 7/1994 | Graf | |
| 5,334,203 A | 8/1994 | Wagner | |
| 5,348,026 A | 9/1994 | Davidson | |
| 5,350,380 A | 9/1994 | Goble et al. | |
| 5,360,448 A | 11/1994 | Thramann | |
| 5,370,697 A | 12/1994 | Baumgartner | |
| 5,401,269 A | 3/1995 | Buttner-Janz et al. | |
| 5,405,390 A | 4/1995 | O'Leary et al. | |
| 5,413,576 A | 5/1995 | Rivard | |
| 5,415,659 A | 5/1995 | Lee et al. | |
| 5,415,661 A | 5/1995 | Holmes | |
| 5,425,773 A | 6/1995 | Boyd et al. | |
| 5,437,669 A | 8/1995 | Yuan et al. | |
| 5,437,672 A * | 8/1995 | Alleyne | 606/279 |
| 5,443,483 A | 8/1995 | Kirsch | |
| 5,445,639 A | 8/1995 | Kuslich et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,470,333 A | 11/1995 | Ray | |
| 5,474,551 A | 12/1995 | Finn et al. | |
| 5,474,555 A | 12/1995 | Puno et al. | |
| 5,491,882 A | 2/1996 | Walston et al. | |
| 5,496,318 A | 3/1996 | Howland et al. | |
| 5,501,684 A | 3/1996 | Schlapfer et al. | |
| 5,507,823 A | 4/1996 | Walston et al. | |
| 5,510,396 A | 4/1996 | Prewett et al. | |
| 5,514,180 A | 5/1996 | Heggeness et al. | |
| 5,527,312 A | 6/1996 | Ray | |
| 5,534,028 A | 7/1996 | Bao et al. | |
| 5,534,030 A | 7/1996 | Navarro et al. | |
| 5,545,229 A | 8/1996 | Parsons et al. | |
| 5,556,431 A | 9/1996 | Buttner-Janz | |
| 5,562,738 A | 10/1996 | Boyd et al. | |
| 5,569,247 A | 10/1996 | Morrison | |
| 5,571,189 A | 11/1996 | Kuslich | |
| 5,571,191 A | 11/1996 | Fitz | |
| 5,575,792 A | 11/1996 | Errico et al. | |
| 5,577,995 A | 11/1996 | Walker et al. | |
| 5,587,695 A | 12/1996 | Warmerdam | |
| 5,599,311 A | 2/1997 | Raulerson | |
| 5,603,713 A | 2/1997 | Aust et al. | |
| 5,609,641 A | 3/1997 | Johnson et al. | |
| 5,643,263 A | 7/1997 | Simonson | |
| 5,645,597 A | 7/1997 | Krapiva | |
| 5,645,599 A | 7/1997 | Samani | |
| 5,649,930 A | 7/1997 | Kertzner | |
| 5,653,762 A | 8/1997 | Pisharodi | |
| 5,658,338 A | 8/1997 | Tullos et al. | |
| 5,662,651 A | 9/1997 | Tornier et al. | |
| 5,672,175 A | 9/1997 | Martin | |
| 5,674,295 A | 10/1997 | Ray et al. | |
| 5,674,296 A | 10/1997 | Bryan et al. | |
| 5,676,701 A | 10/1997 | Yuan et al. | |
| 5,678,317 A | 10/1997 | Stefanakos | |
| 5,683,391 A | 11/1997 | Boyd | |
| 5,683,392 A | 11/1997 | Richelsoph et al. | |
| 5,683,464 A | 11/1997 | Wagner et al. | |
| 5,683,466 A | 11/1997 | Vitale | |
| 5,688,274 A | 11/1997 | Errico et al. | |
| 5,690,630 A | 11/1997 | Errico et al. | |
| 5,700,268 A | 12/1997 | Bertin | |
| 5,702,450 A | 12/1997 | Bisserie | |
| 5,704,941 A | 1/1998 | Jacober et al. | |
| 5,716,415 A | 2/1998 | Steffee | |
| 5,725,527 A | 3/1998 | Biedermann et al. | |
| 5,733,284 A | 3/1998 | Martin | |
| 5,738,585 A | 4/1998 | Hoyt, III et al. | |
| 5,741,255 A | 4/1998 | Krag et al. | |
| 5,741,261 A | 4/1998 | Moskovitz et al. | |
| 5,766,253 A | 6/1998 | Brosnahan, III | |
| 5,776,135 A | 7/1998 | Errico et al. | |
| 5,782,833 A | 7/1998 | Haider | |
| 5,797,911 A | 8/1998 | Sherman et al. | |
| 5,800,433 A | 9/1998 | Benzel et al. | |
| 5,824,093 A | 10/1998 | Ray et al. | |
| 5,824,094 A | 10/1998 | Serhan et al. | |
| 5,827,289 A | 10/1998 | Reiley et al. | |
| 5,836,948 A | 11/1998 | Zucherman et al. | |
| 5,860,977 A | 1/1999 | Zucherman et al. | |
| 5,863,293 A | 1/1999 | Richelsoph | |
| 5,865,846 A | 2/1999 | Bryan et al. | |
| 5,866,113 A | 2/1999 | Hendriks et al. | |
| 5,868,745 A | 2/1999 | Alleyne | |
| 5,879,350 A | 3/1999 | Sherman et al. | |
| 5,879,396 A | 3/1999 | Walston et al. | |
| 5,885,285 A | 3/1999 | Simonson | |
| 5,885,286 A | 3/1999 | Sherman et al. | |
| 5,891,145 A | 4/1999 | Morrison et al. | |
| 5,893,889 A | 4/1999 | Harrington | |
| RE36,221 E | 6/1999 | Breard et al. | |
| 5,947,893 A | 9/1999 | Agrawal et al. | |
| 5,947,965 A | 9/1999 | Bryan | |
| 5,964,760 A | 10/1999 | Richelsoph | |
| 5,984,926 A | 11/1999 | Jones | |
| 6,001,130 A | 12/1999 | Bryan et al. | |
| 6,004,353 A | 12/1999 | Masini | |
| 6,010,503 A | 1/2000 | Richelsoph et al. | |
| 6,014,588 A | 1/2000 | Fitz | |
| 6,019,759 A | 2/2000 | Rogozinski | |
| 6,019,792 A | 2/2000 | Cauthen | |

| | | |
|---|---|---|
| 6,022,350 A | 2/2000 | Ganem |
| 6,039,763 A | 3/2000 | Shelokov |
| 6,048,342 A | 4/2000 | Zucherman et al. |
| 6,050,997 A | 4/2000 | Mullane |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,391 A | 6/2000 | Metz-Stavenhagen et al. |
| 6,077,262 A | 6/2000 | Schläpfer et al. |
| 6,080,157 A | 6/2000 | Cathro et al. |
| 6,086,590 A | 7/2000 | Margulies et al. |
| 6,090,111 A | 7/2000 | Nichols |
| 6,113,600 A | 9/2000 | Drummond et al. |
| 6,113,637 A | 9/2000 | Gill et al. |
| 6,120,510 A | 9/2000 | Albrektsson et al. |
| 6,132,430 A | 10/2000 | Wagner |
| 6,132,462 A | 10/2000 | Li |
| 6,132,464 A | 10/2000 | Martin |
| 6,132,465 A | 10/2000 | Ray et al. |
| 6,165,177 A | 12/2000 | Wilson et al. |
| 6,190,388 B1 | 2/2001 | Michelson et al. |
| 6,193,724 B1 | 2/2001 | Chan |
| 6,193,758 B1 | 2/2001 | Huebner |
| 6,200,322 B1 | 3/2001 | Branch et al. |
| 6,214,012 B1 | 4/2001 | Karpman et al. |
| 6,224,602 B1 | 5/2001 | Hayes |
| 6,231,575 B1 | 5/2001 | Krag |
| 6,248,105 B1 | 6/2001 | Schläpfer et al. |
| 6,280,443 B1 | 8/2001 | Gu et al. |
| 6,290,703 B1 | 9/2001 | Ganem |
| 6,293,949 B1 | 9/2001 | Justis et al. |
| 6,302,890 B1 | 10/2001 | Leone, Jr. |
| 6,309,391 B1 | 10/2001 | Crandall et al. |
| 6,312,431 B1 | 11/2001 | Asfora |
| 6,340,361 B1 | 1/2002 | Kraus et al. |
| 6,340,477 B1 | 1/2002 | Anderson |
| 6,342,054 B1 | 1/2002 | Mata |
| 6,361,506 B1 | 3/2002 | Saenger et al. |
| 6,368,320 B1 | 4/2002 | Le Couedic et al. |
| 6,419,703 B1 | 7/2002 | Fallin et al. |
| 6,440,169 B1 | 8/2002 | Elberg et al. |
| 6,443,954 B1 | 9/2002 | Bramlet et al. |
| 6,451,021 B1 | 9/2002 | Ralph et al. |
| 6,471,705 B1 | 10/2002 | Biedermann et al. |
| 6,514,253 B1 | 2/2003 | Yao |
| 6,520,963 B1 | 2/2003 | McKinley |
| 6,524,315 B1 | 2/2003 | Selvitelli et al. |
| 6,540,749 B2 | 4/2003 | Schäfer et al. |
| 6,547,790 B2 | 4/2003 | Harkey, III et al. |
| 6,554,843 B1 | 4/2003 | Ou |
| 6,565,565 B1 | 5/2003 | Yuan et al. |
| 6,565,572 B2 | 5/2003 | Chappius |
| 6,565,605 B2 | 5/2003 | Goble et al. |
| 6,572,617 B1 | 6/2003 | Senegas |
| 6,579,319 B2 | 6/2003 | Goble et al. |
| 6,585,740 B2 | 7/2003 | Schlapfer et al. |
| 6,585,769 B1 | 7/2003 | Muhanna et al. |
| 6,607,530 B1 | 8/2003 | Carl et al. |
| 6,610,091 B1 * | 8/2003 | Reiley ............. 623/17.11 |
| 6,619,091 B2 | 9/2003 | Heffe |
| 6,623,485 B2 | 9/2003 | Doubler et al. |
| 6,626,909 B2 | 9/2003 | Chin |
| 6,632,226 B2 | 10/2003 | Chan |
| 6,638,281 B2 | 10/2003 | Gorek |
| 6,645,214 B2 | 11/2003 | Brown et al. |
| 6,648,891 B2 | 11/2003 | Kim |
| 6,669,698 B1 | 12/2003 | Tromanhauser et al. |
| 6,669,729 B2 | 12/2003 | Chin |
| 6,712,818 B1 | 3/2004 | Michelson |
| 6,712,849 B2 | 3/2004 | Re et al. |
| 6,736,815 B2 | 5/2004 | Ginn |
| 6,749,361 B2 | 6/2004 | Hermann et al. |
| 6,761,698 B2 | 7/2004 | Shibata et al. |
| 6,761,720 B1 | 7/2004 | Senegas |
| 6,770,095 B2 | 8/2004 | Grinberg et al. |
| 6,783,527 B2 | 8/2004 | Drewry et al. |
| 6,790,233 B2 | 9/2004 | Brodke et al. |
| 6,793,678 B2 | 9/2004 | Hawkins |
| 6,802,844 B2 | 10/2004 | Ferree |
| 6,811,567 B2 | 11/2004 | Reiley |
| 6,902,567 B2 | 6/2005 | Del Medico |
| 6,902,580 B2 | 6/2005 | Fallin et al. |
| 6,908,465 B2 | 6/2005 | von Hoffmann et al. |
| 6,949,123 B2 | 9/2005 | Reiley |
| 6,974,478 B2 | 12/2005 | Reiley |
| 6,979,299 B2 | 12/2005 | Peabody et al. |
| 7,011,658 B2 | 3/2006 | Young |
| 7,044,969 B2 | 5/2006 | Errico et al. |
| 7,051,451 B2 | 5/2006 | Augostino et al. |
| 7,220,262 B1 | 5/2007 | Hynes |
| 7,291,150 B2 * | 11/2007 | Graf ............. 606/86 A |
| 7,294,127 B2 | 11/2007 | Leung et al. |
| 7,302,288 B1 | 11/2007 | Schellenberg |
| 7,309,338 B2 | 12/2007 | Cragg |
| 7,445,635 B2 | 11/2008 | Fallin et al. |
| 7,455,685 B2 | 11/2008 | Justis |
| 7,547,324 B2 | 6/2009 | Cragg et al. |
| 7,691,145 B2 * | 4/2010 | Reiley et al. ............. 623/17.11 |
| 2001/0012938 A1 | 8/2001 | Zucherman et al. |
| 2001/0020170 A1 | 9/2001 | Zucherman et al. |
| 2002/0013585 A1 | 1/2002 | Gournay et al. |
| 2002/0013588 A1 | 1/2002 | Landry et al. |
| 2002/0029039 A1 | 3/2002 | Zucherman et al. |
| 2002/0042613 A1 | 4/2002 | Mata |
| 2002/0049446 A1 | 4/2002 | Harkey, III et al. |
| 2002/0052603 A1 | 5/2002 | Nichols et al. |
| 2002/0065557 A1 | 5/2002 | Goble et al. |
| 2002/0068975 A1 | 6/2002 | Teitelbaum et al. |
| 2002/0082601 A1 | 6/2002 | Toyama et al. |
| 2002/0120272 A1 | 8/2002 | Yuan et al. |
| 2002/0123752 A1 | 9/2002 | Schultheiss et al. |
| 2002/0123806 A1 | 9/2002 | Reiley |
| 2002/0151895 A1 | 10/2002 | Soboleski et al. |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0069603 A1 | 4/2003 | Little et al. |
| 2003/0125740 A1 | 7/2003 | Khanna |
| 2003/0181914 A1 | 9/2003 | Johnson et al. |
| 2003/0191532 A1 | 10/2003 | Goble et al. |
| 2003/0195631 A1 | 10/2003 | Ferree |
| 2003/0204259 A1 | 10/2003 | Goble et al. |
| 2003/0204261 A1 | 10/2003 | Eisermann et al. |
| 2003/0233148 A1 | 12/2003 | Ferree |
| 2004/0006391 A1 | 1/2004 | Reiley |
| 2004/0049205 A1 | 3/2004 | Lee et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0111154 A1 | 6/2004 | Reiley |
| 2004/0116927 A1 | 6/2004 | Graf |
| 2004/0127989 A1 | 7/2004 | Dooris et al. |
| 2004/0143264 A1 | 7/2004 | McAfee |
| 2004/0204710 A1 | 10/2004 | Patel et al. |
| 2004/0204718 A1 | 10/2004 | Hoffman |
| 2004/0230201 A1 | 11/2004 | Yuan et al. |
| 2004/0230304 A1 | 11/2004 | Yuan et al. |
| 2004/0260305 A1 | 12/2004 | Gorensek et al. |
| 2004/0267279 A1 | 12/2004 | Casutt et al. |
| 2005/0010291 A1 | 1/2005 | Stinson et al. |
| 2005/0015146 A1 | 1/2005 | Louis et al. |
| 2005/0027359 A1 | 2/2005 | Mashburn |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0043799 A1 | 2/2005 | Reiley |
| 2005/0049705 A1 | 3/2005 | Hale et al. |

| | | | |
|---|---|---|---|
| 2005/0055096 A1 | 3/2005 | Serhan et al. | |
| 2005/0059972 A1 | 3/2005 | Biscup | |
| 2005/0080428 A1 | 4/2005 | White | |
| 2005/0080486 A1 | 4/2005 | Fallin et al. | |
| 2005/0085912 A1 | 4/2005 | Arnin et al. | |
| 2005/0101956 A1 | 5/2005 | Simonson | |
| 2005/0102028 A1 | 5/2005 | Arnin et al. | |
| 2005/0119748 A1 | 6/2005 | Reiley et al. | |
| 2005/0131406 A1 | 6/2005 | Reiley et al. | |
| 2005/0131409 A1 | 6/2005 | Chervitz et al. | |
| 2005/0131537 A1 | 6/2005 | Hoy et al. | |
| 2005/0131538 A1 | 6/2005 | Chervitz et al. | |
| 2005/0131545 A1 | 6/2005 | Chervitz et al. | |
| 2005/0137705 A1 | 6/2005 | Reiley | |
| 2005/0137706 A1 | 6/2005 | Reiley | |
| 2005/0143818 A1 | 6/2005 | Yuan et al. | |
| 2005/0149190 A1 | 7/2005 | Reiley | |
| 2005/0159746 A1 | 7/2005 | Grob et al. | |
| 2005/0165484 A1 | 7/2005 | Ferree et al. | |
| 2005/0177240 A1 | 8/2005 | Blain | |
| 2005/0187560 A1 | 8/2005 | Dietzel et al. | |
| 2005/0192589 A1 | 9/2005 | Raymond et al. | |
| 2005/0222683 A1 | 10/2005 | Berry | |
| 2005/0228500 A1 | 10/2005 | Kim et al. | |
| 2005/0234552 A1 | 10/2005 | Reiley | |
| 2005/0240264 A1 | 10/2005 | Tokish, Jr. et al. | |
| 2005/0240265 A1 | 10/2005 | Kuiper et al. | |
| 2005/0240266 A1 | 10/2005 | Kuiper et al. | |
| 2005/0251256 A1 | 11/2005 | Reiley | |
| 2005/0261770 A1 | 11/2005 | Kuiper et al. | |
| 2005/0267579 A1 | 12/2005 | Reiley et al. | |
| 2005/0273167 A1 | 12/2005 | Triplett et al. | |
| 2005/0277922 A1 | 12/2005 | Trieu et al. | |
| 2005/0283238 A1 | 12/2005 | Reiley | |
| 2006/0009847 A1 | 1/2006 | Reiley | |
| 2006/0009848 A1 | 1/2006 | Reiley | |
| 2006/0009849 A1 | 1/2006 | Reiley | |
| 2006/0025769 A1 | 2/2006 | Dick et al. | |
| 2006/0029186 A1 | 2/2006 | De Villiers et al. | |
| 2006/0036246 A1 | 2/2006 | Carl et al. | |
| 2006/0041311 A1 | 2/2006 | McLeer | |
| 2006/0041314 A1 | 2/2006 | Millard | |
| 2006/0052785 A1 | 3/2006 | Augostino et al. | |
| 2006/0058790 A1 | 3/2006 | Carl et al. | |
| 2006/0058791 A1 | 3/2006 | Broman et al. | |
| 2006/0079895 A1 | 4/2006 | McLeer | |
| 2006/0085010 A1 | 4/2006 | Lieberman | |
| 2006/0085072 A1 | 4/2006 | Funk et al. | |
| 2006/0085075 A1 | 4/2006 | McLeer | |
| 2006/0100707 A1 | 5/2006 | Stinson et al. | |
| 2006/0100709 A1 | 5/2006 | Reiley et al. | |
| 2006/0122703 A1 | 6/2006 | Aebi et al. | |
| 2006/0149375 A1 | 7/2006 | Yuan et al. | |
| 2006/0184180 A1 | 8/2006 | Augostino et al. | |
| 2006/0241532 A1 | 10/2006 | Murakami | |
| 2006/0265070 A1 | 11/2006 | Stinson et al. | |
| 2007/0079517 A1 | 4/2007 | Augostino et al. | |
| 2007/0088358 A1 | 4/2007 | Yuan et al. | |
| 2007/0093833 A1 | 4/2007 | Kuiper et al. | |
| 2007/0168029 A1 | 7/2007 | Yuan et al. | |
| 2007/0233256 A1 | 10/2007 | Ohrt et al. | |
| 2007/0255411 A1 | 11/2007 | Reiley | |
| 2007/0265706 A1 | 11/2007 | Reiley et al. | |
| 2007/0276370 A1 | 11/2007 | Altarac et al. | |
| 2007/0276374 A1 | 11/2007 | Broman et al. | |
| 2007/0282445 A1 | 12/2007 | Reiley | |
| 2008/0015583 A1 | 1/2008 | Reiley | |
| 2008/0015696 A1 | 1/2008 | Reiley | |

FOREIGN PATENT DOCUMENTS

| | | | |
|---|---|---|---|
| DE | 10312755 A1 | 10/2003 | |
| EP | 1103226 | 5/2001 | |
| EP | 1205152 A1 | 5/2002 | |
| EP | 1254639 A1 | 11/2002 | |
| FR | 2726459 | 5/1996 | |
| FR | 2749155 | 12/1997 | |
| FR | 2844180 | 3/2004 | |
| IE | S970323 | 6/1998 | |
| JP | 59010807 A | 1/1984 | |
| JP | 10082605 A | 3/1998 | |
| JP | 10179622 A | 7/1998 | |
| WO | WO 95/05783 A1 | 3/1995 | |
| WO | WO 96/00049 A1 | 1/1996 | |
| WO | WO 98/48717 A1 | 11/1998 | |
| WO | WO 98/56301 A1 | 12/1998 | |
| WO | WO 99/05995 A1 | 2/1999 | |
| WO | WO 99/23963 A1 | 5/1999 | |
| WO | WO 99/60957 A1 | 12/1999 | |
| WO | WO 99/65412 A1 | 12/1999 | |
| WO | WO 00/38582 A1 | 7/2000 | |
| WO | WO 00/62684 A1 | 10/2000 | |
| WO | WO 01/06939 A1 | 2/2001 | |
| WO | WO 01/15638 A1 | 3/2001 | |
| WO | WO 01/28442 A1 | 4/2001 | |
| WO | WO 01/30248 A1 | 5/2001 | |
| WO | WO 01/39678 A1 | 6/2001 | |
| WO | WO 01/67972 A2 | 9/2001 | |
| WO | WO 01/97721 A2 | 12/2001 | |
| WO | WO 02/00270 A1 | 1/2002 | |
| WO | WO 02/00275 A1 | 1/2002 | |
| WO | WO 02/02024 A1 | 1/2002 | |
| WO | WO 02/02158 A1 | 1/2002 | |
| WO | WO 02/34150 A2 | 5/2002 | |
| WO | WO02/43603 | * 6/2002 | .................... 606/247 |
| WO | WO 02/43603 A1 | 6/2002 | |
| WO | WO 02/071960 A1 | 9/2002 | |
| WO | WO 02/089712 A1 | 11/2002 | |
| WO | WO 03/020143 A1 | 3/2003 | |
| WO | WO 03/041618 A2 | 5/2003 | |
| WO | WO 03/075805 A1 | 9/2003 | |
| WO | WO 03/101350 A1 | 12/2003 | |
| WO | WO 2004/071358 A1 | 8/2004 | |
| WO | WO 2004/103227 A1 | 12/2004 | |
| WO | WO 2004/103228 A1 | 12/2004 | |
| WO | WO 2005/009301 A1 | 2/2005 | |
| WO | WO 2005/079711 A1 | 9/2005 | |

OTHER PUBLICATIONS

Hewko, Brian; U.S. Appl. No. 12/377,552 entitled "Spinal implant," filed Feb. 13, 2009.

Abraham, D.J. et al. "Indications and Trends in Use in Cervical Spinal Fusions." Orthop Clin North Am. Oct. 1998; 29(4):731-44.

Eichholz, K.M. et al. "Complications of Revision Spinal Surgery", Neurosurg Focus; (Sep. 15, 2003), 15(3): pp. 1-4.

Farfan, H.F. Effects of Torsion on the Intervertebral Joints. The Canadian Journal of Surgery, Jul. 1969; 12(3):336-41.

Farfan, H.F. et al. "The Relation of Facet Orientation to Intervertebral Disc Failure." The Canadian Journal of Surgery, Apr. 1967; 10(2):179-85.

Farfan, H.F. The Pathological Anatomy of Degenerative Spondylolisthesis. A Cadaver Study. Spine. Sep.-Oct. 1980; 5(5):412-8.

Fosbinder, R.A. et al. Essentials of Radiologic Science. The McGraw-Hill Companies; 2002.

Goh, J.C. et al. "Influence of PLIF cage size on lumbar spine stability." Spine. Jan. 2000, 25(1) Medline abstract (one page).

Guyer R. et al. "Impliant: Motion Preservation through Total Posterior-Element Replacement." May 7, 2004 Presentation held at Hofburg Center, Vienna, Austria, (2 pages).

Head, W.C. "Wagner surface replacement arthroplasty of the hip." Analysis of fourteen failures in forty-one hips. J Bone Joint Surg. Am; Mar. 1981, 63(3), Medline abstract (one page).

Khoo, L.T. et al. "A biomechanical analysis of the effects of lumbar fusion on the adjacent vetebral motion segment." Proceedings of the 2000 Annual Meeting of the North American Spine Society, New Orleans, pp. 127-128.

Kirkaldy-Willis, W.H. et al. "Pathology and Pathogenesis of Lumbar Spondylosis and Stenosis." Spine. Dec. 1978; 3(4):319-28.

Kotani, Y. et al. The effects of spinal fixation and destabilization on the biomechanical and histologic properties of spinal ligaments. An in vivo study. Spine, Mar. 15, 1998, 23(6), Medline abstract (2 pages).

Kulkarni, et al. "Accelerated Spondylotic Changes Adjacent to the Fused Segment Following Central Cervical Corpectomy: Magnetic Resonance Imaging Study Evidence." J. Neurosurg (Spine 1). 2004; 100: 2-6.

Lam, K. N., et al. X-ray "Diagnosis: A Physician's Approach." Springer-Verlag; 1998.

Lemaire, J.P. et al. "Intervertebral disc prosthesis: results and prospects for the year 2000." Clinical Orthopaedics and Related Research. 1997; No. 337, pp. 64-76.

Lombardi, J.S. et al. "Treatment of Degenerative Spondylolisthesis." Spine. 1985; 10(9): 821-7.

McMillin, C. R. et al. Artificial Spinal Discs with up to Five Years Follow-up. 20th Annual Meeting of the Society for Biomaterials (Abstract) 1994; p. 89.

Nagata, H. et al. "The effects of immobilization of long segments of the spine on the adjacent and distal facet force and lumbrosacral motion". Spine, Dec. 1993; 18(16):2471-2479, (9 pages).

Nibu, K. et al. "Multidirectional stabilizing potential of BAK interbody spinal fusion system for anterior surgery." J Spinal Discord, Aug. 1997; 10(4), Medline abstract (one page).

Posner, I. et al. A "Biomechanical Analysis of the Clinical Stability of the Lumbar and Lumbosacral Spine." Spine. 1982; 7(4): 374-389.

Rosenberg, N.J. "Degenerative Spondylolisthesis. Predisposing Factors." The Journal of Bone and Joint Surgery. 1975; 57-A(4): 467-74.

Sacher, R., Impliant Brochure for presentation at MedTech Insight Conference (Oct. 31, 2003) Boston, MA. pp. 93-94.

Slone, R. M. et al. Body CT: A Practical Approach. The McGraw-Hill Companies; 1999.

Stout, G. H. et al. X-Ray Structure Determination: A Practical Guide. 2nd Edition. John Wiley & Sons; 1989.

Szpalski, M., et al. Spine Arthroplasty: A Historical Review. Eur Spine J. 2002; 11(Suppl. 2): S65-S84.

Tsantrizos, A. et al. "Segmental stability and compressive strength of posterior lumbar interbody fusion implants." Spine, Aug. 1, 2000; 25(15), Medline abstract (one page).

UCR Pedicle Screw System from SeaSpine (information available at http://www.seaspine.com/UCR_Pedicle_Screw_System.html). Accessed Dec. 5, 2005.

Victrex of Lancashire, Great Britain. (information on Victrex available at http://www.matweb.com). Accessed Dec. 5, 2005.

Berg, et al; U.S. Appl. No. 11/800,895 entitled "Minimally Invasive Spine Restoration Systems, Devices, Methods, and Kits," filed May 7, 2007.

Reiley et al; U.S. Appl. No. 11/577,923 entitled "Facet Joint Prostheses" filed Apr. 25, 2007.

Kuiper et al; U.S. Appl. No. 11/577,964 entitled "Crossbar Spinal Prosthesis Having a Modular Design and Systems for Treating Spinal Pathologies," filed Apr. 25, 2007.

Kuiper et al; U.S. Appl. No. 11/577,967 entitled "Crossbar Spinal Prosthesis having a Modular Design and Systems for Treating Spinal Pathologies," filed Apr. 25, 2007.

Reiley, Mark; U.S. Appl. No. 11/831,870 entitled "Prostheses systems and methods for replacement of natural facet joints with artificial facet joint surfaces," filed Jul. 31, 2007.

Ralph et al; U.S. Appl. No. 11/837,335 entitled "Angled Washer Polyaxial Connection for Dynamic Spine Prosthesis," filed Aug. 10, 2007.

Stone et al; U.S. Appl. No. 11/861,239 entitled "Facet Replacement Device Removal and Revision Systems and Methods" filed Sep. 25, 2007.

McLeer, Thomas, U.S. Appl. No. 11/934,724 entitled "Polymeric Joint Complex and Methods of Use" filed Nov. 2, 2007.

McLeer, Thomas, U.S. Appl. No. 11/934,720 entitled "Polymeric Joint Complex and Methods of Use" filed Nov. 2, 2007.

McLeer, Thomas, U.S. Appl. No. 11/934,719 entitled "Polymeric Joint Complex and Methods of Use" filed Nov. 2, 2007.

Reiley, Mark, U.S. Appl. No. 11/934,713 entitled "Facet arthroplasty devices and methods" filed Nov. 2, 2007.

Reiley, Mark, U.S. Appl. No. 11/939,540 entitled "Facet arthroplasty devices and methods" filed Nov. 13, 2007.

Reiley, Mark, U.S. Appl. No. 11/943,458 entitled "Facet arthroplasty devices and methods" filed Nov. 20, 2007.

Reiley, Mark, U.S. Appl. No. 11/949,007 entitled "Facet arthroplasty devices and methods" filed Nov. 30, 2007.

Reiley, Mark, U.S. Appl. No. 11/949,000 entitled "Facet arthroplasty devices and methods" filed Nov. 30, 2007.

Reiley et al.; U.S. Appl. No. 11/948,963 entitled "Prostheses, systems and methods for replacement of natural facet joints with artificial facet joint surfaces" filed Nov. 30, 2007.

Reiley, Mark, U.S. Appl. No. 11/957,208 entitled "Facet arthroplasty devices and methods" filed Dec. 14, 2007.

Reiley et al.; U.S. Appl. No. 11/957,315 entitled "Prostheses, systems and methods for replacement of natural facet joints with artificial facet joint surfaces" filed Dec. 14, 2007.

Reiley, Mark; U.S. Appl. No. 11/957,175 entitled "Facet arthroplasty devices and methods" filed Dec. 14, 2007.

Reiley et al.; U.S. Appl. No. 11/957,290 entitled "Prostheses, systems and methods for replacement of natural facet joints with artificial facet joint surfaces" filed Dec. 14, 2007.

Reiley, Mark; U.S. Appl. No. 11/956,961 entitled "Facet arthroplasty devices and methods" filed Dec. 14, 2007.

Reiley, Mark; U.S. Appl. No. 11/957,149 entitled "Facet arthroplasty devices and methods" filed Dec. 14, 2007.

Reiley, Mark; U.S. Appl. No. 11/957,061 entitled "Facet arthroplasty devices and methods" filed Dec. 14, 2007.

Reiley et al.; U.S. Appl. No. 11/957,259 entitled "Prostheses, systems and methods for replacement of natural facet joints with artificial facet joint surfaces" filed Dec. 14, 2007.

Reiley, Mark; U.S. Appl. No. 12/016,177 entitled "Facet arthroplasty devices and methods" filed Jan. 17, 2008.

Kuiper et al.; U.S. Appl. No. 11/948,994 entitled "Crossbar spinal prosthesis having a modular design and related implantation methods" filed Nov. 30, 2007.

Kuiper et al.; U.S. Appl. No. 11/948,973 entitled "Crossbar spinal prosthesis having a modular design and related implantation methods" filed Nov. 30, 2007.

Kuiper et al.; U.S. Appl. No. 11/957,303 entitled "Crossbar spinal prosthesis having a modular design and related implantation methods" filed Nov. 30, 2007.

McLeer, Thomas; U.S. Appl. No. 11/952,988 entitled "Polymeric joint complex and methods of use" filed Dec. 7, 2007.

Yuan et al.; U.S. Appl. No. 12/027,899 entitled "Prostheses, tools and methods for replacement of natural facet joints with artificial facet joint surfaces," filed Feb. 7, 2008.

Reiley et al; U.S. Appl. No. 12/058,403 entitled "Polyaxial adjustment of facet joint prostheses," filed Mar. 28, 2008.

Quest et al.; U.S. Appl. No. 12/099,068 entitled "Measurement and trialing system and methods for orthopedic device component selection," filed Apr. 7, 2008.

Reiley, Mark; U.S. Appl. No. 12/176,280 entitled "Facet arthroplasty devices and methods," filed Jul. 18, 2008.

Yuan et al; U.S. Appl. No. 12/163,738 entitled "Prostheses, tools and methods for replacement of natural joints with artificial facet joint surfaces," filed Jun. 27, 2008.

Funk et al; U.S. Appl. No. 12/186,461 entitled "Implantable orthopedic device component selection instrument and methods," filed Aug. 5, 2008.

* cited by examiner

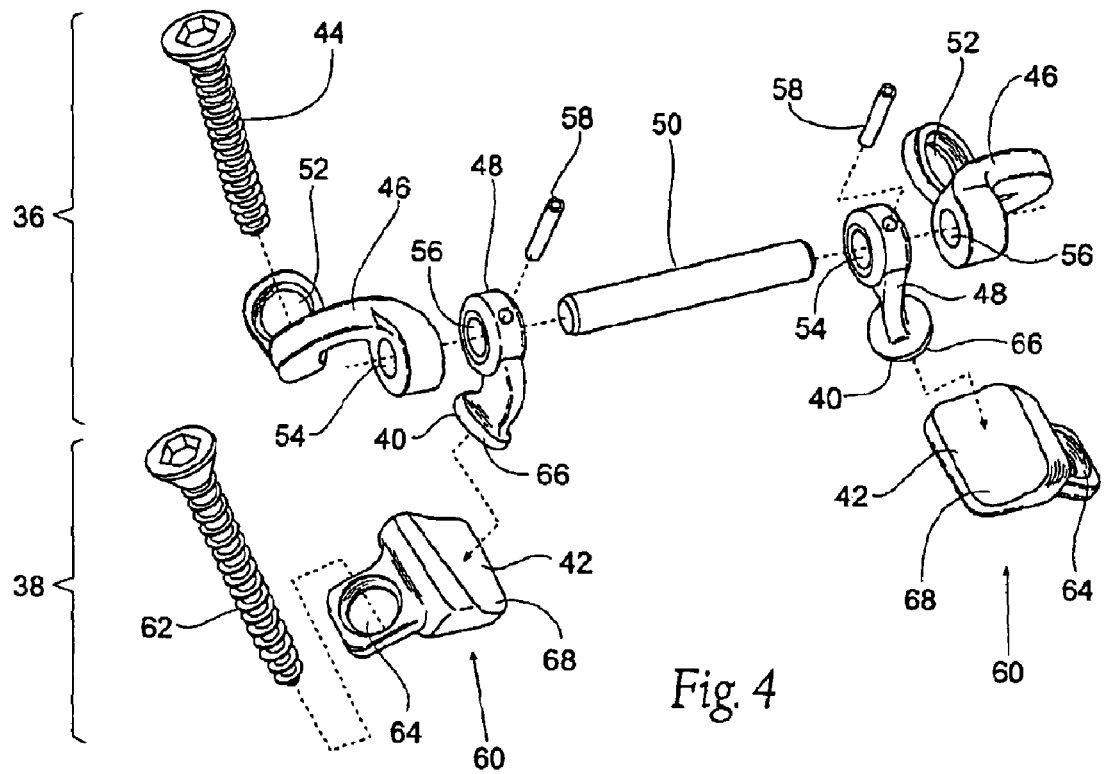
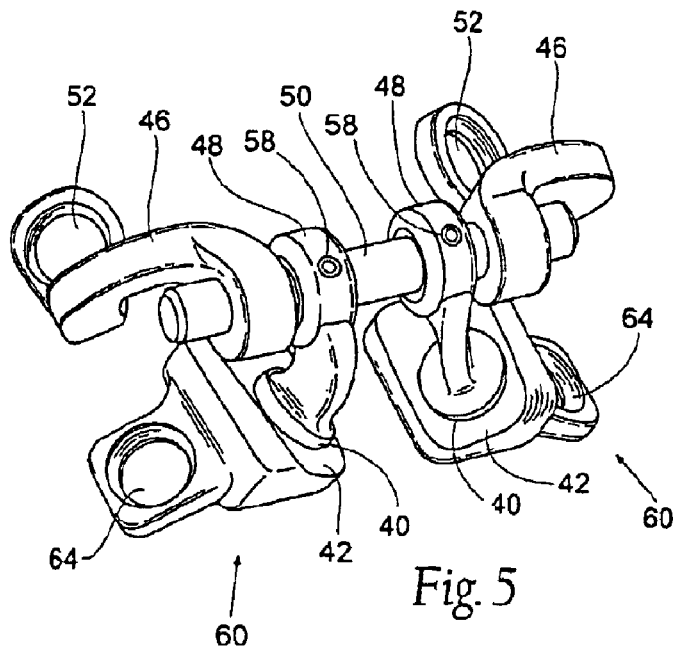

FACET JOINT PROSTHESES

CROSS-REFERENCE TO RELATED APPLICATIONS

This application is the national stage under 35 USC §371 of International Application No. PCT/US2005/038087, filed Oct. 21, 2005, entitled "Facet Joint Prostheses," which international application claims priority under 35 USC §120 to the following:

U.S. patent application Ser. No. 10/974,009 filed Oct. 25, 2004, entitled "Prostheses, Systems and Method for Replacement of Natural Facet Joints with Artificial Facet Joint Surfaces;" and U.S. patent application Ser. No. 11/122,271, filed May 3, 2005, entitled "Crossbar Spinal Prosthesis Having a Modular Design and Related Implantation Methods," which is a continuation-in-part of U.S. patent application Ser. No. 11/071,541 filed Mar. 2, 2005, entitled "Crossbar Spinal Prosthesis Having a Modular Design and Related Implantation Methods," which, in turn, is a continuation-in-part of U.S. patent application Ser. No. 10/831,657, filed Apr. 22, 2004, entitled "Anti-Rotation Fixation Element for Spinal Prosthesis;" which claims priority under 35 USC §119 from the following patent applications: U.S. Patent Applications No. 60/602,827 to McLeer, filed Aug. 18, 2004, entitled "Articulating Mechanism Locking Device"; No. 60/642,321 to Funk et al., filed Jan. 7, 2005, entitled "Component Selection Instrument"; No. 60/642,250 to Charbonneau et al., filed Jan. 7, 2005, entitled "Bearing Surface Preloader"; No. 60/643,556 to McLeer, filed Jan. 13, 2005, entitled "Motion Lock Cable Device"; No. 60/650,302 to Ralph et al., filed Feb. 4, 2005, entitled "Facet Joint Replacement Tools"; this application also claims the benefit under 35 U.S.C. §119 of U.S. Patent Application No. 60/567,972 to Reiley et al., filed May 3, 2004, entitled "Spinal Prosthesis for Facet Joint Replacement." The disclosures of these patent applications are all incorporated herein by reference as if fully set forth herein.

FIELD OF THE INVENTION

This invention relates to prostheses for treating various types of spinal pathologies, as well as to methods of treating spinal pathologies. This invention also relates to systems and kits for treating spinal pathologies. The systems and kits include intervertebral discs prosthesis and facet joint prosthesis.

BACKGROUND OF THE INVENTION

I. Vertebral Anatomy

As FIG. 1 shows, the human spinal column 10 is comprised of a series of thirty-three stacked vertebrae 12 divided into five regions. The cervical region includes seven vertebrae 12, known as C1-C7. The thoracic region includes twelve vertebrae 12, known as T1-T12. The lumbar region contains five vertebrae 12, known as T1-T5. The sacral region is comprised of five vertebrae 12, known as S1-S5. The coccygeal region contains four vertebrae 12, known as Co1-Co4.

FIG. 2 shows a normal human lumbar vertebra 12. Although the lumbar vertebrae 12 vary somewhat according to location, they share many features common to most vertebrae 12. Each vertebra 12 includes a vertebral body 14. Two short bones, the pedicles 16, extend backward from each side of the vertebral body 14 to form a vertebral arch 18.

At the posterior end of each pedicle 16 the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 into the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side from the union of the pedicle 16 with the lamina 20. The inferior processes 28 are oval plates of bone that jut downward on each side.

The superior and inferior articular processes 26 and 28 each have a natural bony structure known as a facet. The superior articular facet 30 faces upward, while the inferior articular facet 31 faces downward. As FIG. 3 shows, when adjacent vertebrae 12 are aligned, the facets 30 and 31, capped with a smooth articular cartilage, interlock to form a facet joint 32, also known as a zygapopysial joint.

The facet joint 32 is composed of a superior facet and an inferior facet. The superior facet is formed by the vertebral level below the joint 32, and the inferior facet is formed by the vertebral level above the joint 32. For example, in the L4-L5 facet joint, the superior facet of the joint is formed by bony structure on the L-5 vertebra (e.g., a superior articular surface and supporting bone on the L-5 vertebra), and the inferior facet of the joint is formed by bony structure on the L-4 vertebra (e.g., an inferior articular surface and supporting bone on the L-4 vertebra).

As also shown in FIG. 3, an intervertebral disc 34 positioned between each pair of vertebrae 12 permits gliding movement between the vertebrae 12. Thus, the structure and alignment of the vertebrae 12 permit a range of movement of the vertebrae 12 relative to each other.

II. Facet Joint Dysfunction

Back pain, particularly in the "small of the back", or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called a "pinched" nerve, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is spinal fusion. Another method of stabilization is fixation of any number of vertebrae to stabilize and prevent movement of the vertebrae.

Another type of conventional treatment is decompressive laminectomy. This procedure involves excision of the laminae and/or soft tissues of the spine to relieve compression of nerves.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit a person's mobility.

SUMMARY OF THE INVENTION

There is a need for prostheses, systems, and methods that overcome the problems and disadvantages associated with current strategies and designs in various treatments for spine pathologies.

The invention provides prostheses, devices, systems, kits and methods designed to replace natural facet joints and/or part of the lamina at virtually all spinal levels including L1-L2, L2-L3, L3-L4, L4-L5, L5-S1, T11-T12, and T12-L1. The prostheses, systems, and methods can restore a desired anatomy to a spine and give back to an individual a desired range of mobility. The prostheses, systems, and methods also can lessen or alleviate spinal pain by relieving the source nerve compression or impingement.

For the sake of description, the prostheses that embody features of the invention will be called either "cephalad" or "caudal" with relation to the portion of a given natural facet joint they replace. As previously described, a given natural facet joint has a superior facet and an inferior facet. In anatomical terms, the superior facet of the joint is formed by the vertebral level below the joint (which can thus be called the caudal portion of the facet joint, i.e., because it is near the feet). The inferior facet of the joint is formed by the vertebral level above the joint (which can thus be called the cephalad portion of the facet joint, i.e., because it is near the head). Thus, a prosthesis that, in use, replaces the caudal portion of a facet joint (i.e., the superior facet) will be called a "caudal" prosthesis. Likewise, a prosthesis that, in use, replaces the cephalad portion of a facet joint (i.e., the inferior facet) will be called a "cephalad" prosthesis.

One aspect of the invention provides a facet joint prosthesis to replace, on a vertebral body, a caudal portion of a natural facet joint (e.g., a superior articular surface and supporting bone structure on the vertebral body). A pair of fixation elements are adapted to be secured within the vertebral body in an orientation that best assures a secure and durable attachment to cortical and/or cancellous bone. Artificial facet joint structures mounted on the fixation elements. In one embodiment, the artificial facet joint structure is mounted on the fixation element by use of a support. The artificial facet joint structures articulate with a complementary natural or artificial facet joint structure. The artificial facet joint structures may by coupled by a brace to further secure and stabilize the prosthesis.

This aspect of the invention also provides a method of replacing, on a vertebral body, a caudal portion of a natural facet joint. The method removes a caudal portion of the natural facet joint from the vertebral body. Right and left fixation elements are secured within the vertebral body, e.g., to right and left pedicles respectively. An artificial facet joint structure is mounted on each fixation elements. A brace may be coupled to each of the artificial facet joint structures to stabilize the prosthesis.

Another aspect of the invention provides a facet joint prosthesis to replace, on a vertebral body, a cephalad portion of a natural facet joint (e.g., an inferior articular surface and supporting bone structure on the vertebral body). A pair of fixation elements are adapted to be secured within the vertebral body in an orientation that best assures a secure and durable attachment to cortical and/or cancellous bone. In a preferred embodiment, arms are adapted to be mounted on the fixation elements (e.g., using a brace and/or support). The arms carry an artificial facet joint structure for articulation with a complementary natural or artificial facet joint structure. The arms may by coupled by a brace to further secure and stabilize the prosthesis.

This aspect of the invention also provides a method of replacing, on a vertebral body, a cephalad portion of a natural facet joint. The method removes a cephalad portion of the natural facet joint from the vertebral body. In one embodiment, right and left fixation elements are secured within the vertebral body, e.g., to the right and left pedicles respectively. A support is mounted on each fixation element. A brace carrying right and left arms (carrying the artificial facet joint structures) is coupled to the supports.

In an alternative embodiment, right and left fixation elements are secured within the vertebral body, e.g., to the right and left pedicles respectively. A support is mounted on each fixation element. An arm, carrying an artificial facet joint structure, is mounted on each support. A brace may be coupled to each of the arms to stabilize the prosthesis.

Another aspect of the invention provides a facet joint prosthesis to replace, on a vertebral body, a caudal portion of a natural facet joint, including: a support component adapted to span a portion of the vertebral body and to support prosthetic caudal facet elements; and a pair of prosthetic caudal facet elements adjustable relative to the support component and adapted to replace the caudal portion of the natural facet joint.

Yet another aspect of the invention provides a prosthesis for replacing a natural spinal facet joint including: a pair of prosthetic caudal facet elements configured to replace the caudal portion of the natural facet joint; and a modular cephalad prosthesis configured to articulate with the caudal facet elements, the modular cephalad prosthesis comprising a pair of arms, a pair of supports, and a brace extending between the arms and the supports, each of the supports having an articulating portion adapted to articulate with the caudal facet elements.

Still another aspect of the invention provides a prosthesis for replacing a natural spinal facet joint comprising: a modular caudal prosthesis comprising a pair of prosthetic caudal facet elements configured to replace the caudal portion of the natural facet joint and a caudal brace extending between the caudal facet elements; and a modular cephalad prosthesis configured to articulate with the caudal facet elements, the modular cephalad prosthesis comprising a pair of arms, a pair of supports, and a cephalad brace extending between the arms and the supports, each of the supports having an articulating portion adapted to articulate with the caudal facet elements.

Another aspect of the invention provides a system for treating spinal pathologies including an intervertebral disc prosthesis in combination with a facet joint prosthesis comprising a support component adapted to span a portion of the vertebral body and to support prosthetic caudal facet elements; and a pair of prosthetic caudal facet elements adjustable relative to the support component and adapted to replace the caudal portion of the natural facet joint.

Yet another aspect of the invention provides a system for treating spinal pathologies including an intervertebral disc prosthesis in combination with a facet joint prosthesis comprising a pair of prosthetic caudal facet elements configured to replace the caudal portion of the natural facet joint; and a modular cephalad prosthesis configured to articulate with the caudal facet elements, the modular cephalad prosthesis comprising a pair of arms, a pair of supports, and a brace extending between the arms and the supports, each of the supports having an articulating portion adapted to articulate with the caudal facet elements.

Still another aspect of the invention provides a system for treating spinal pathologies including an intervertebral disc prosthesis in combination with a facet joint prosthesis comprising a modular caudal prosthesis comprising a pair of prosthetic caudal facet elements configured to replace the caudal portion of the natural facet joint and a caudal brace extending between the caudal facet elements; and a modular cephalad prosthesis configured to articulate with the caudal facet elements, the modular cephalad prosthesis comprising a pair of arms, a pair of supports, and a cephalad brace extending between the arms and the supports, each of the supports having an articulating portion adapted to articulate with the caudal facet elements.

Another aspect of the invention provides a surgical kit for treating spinal pathologies including an intervertebral disc prosthesis and a facet joint prosthesis comprising a support component adapted to span a portion of the vertebral body and to support prosthetic caudal facet elements; and a pair of prosthetic caudal facet elements adjustable relative to the support component and adapted to replace the caudal portion of the natural facet joint.

Yet another aspect of the invention provides a surgical kit for treating spinal pathologies including an intervertebral disc prosthesis in combination with a facet joint prosthesis comprising a pair of prosthetic caudal facet elements configured to replace the caudal portion of the natural facet joint; and a modular cephalad prosthesis configured to articulate with the caudal facet elements, the modular cephalad prosthesis comprising a pair of arms, a pair of supports, and a brace extending between the arms and the supports, each of the supports having an articulating portion adapted to articulate with the caudal facet elements.

Still another aspect of the invention provides a surgical kit for treating spinal pathologies including an intervertebral disc prosthesis in combination with a facet joint prosthesis comprising a modular caudal prosthesis comprising a pair of prosthetic caudal facet elements configured to replace the caudal portion of the natural facet joint and a caudal brace extending between the caudal facet elements; and a modular cephalad prosthesis configured to articulate with the caudal facet elements, the modular cephalad prosthesis comprising a pair of arms, a pair of supports, and a cephalad brace extending between the arms and the supports, each of the supports having an articulating portion adapted to articulate with the caudal facet elements.

Other features and advantages of the inventions are set forth in the following Description and Drawings, as well as in the appended claims.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 4 is an exploded perspective view of cephalad and caudal prostheses for replacing, respectively, the inferior and superior halves of a natural facet joint.

FIG. 5 is an assembled perspective view of the prostheses shown in FIG. 4

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE INVENTION

Although the disclosure hereof is detailed and exact to enable those skilled in the art to practice the invention, the physical embodiments herein disclosed merely exemplify the invention that may be embodied in other specific structures. While the preferred embodiment has been described, the details may be changed without departing from the invention, which is defined by the claims.

I. Vertebral Prostheses

Figure 1:
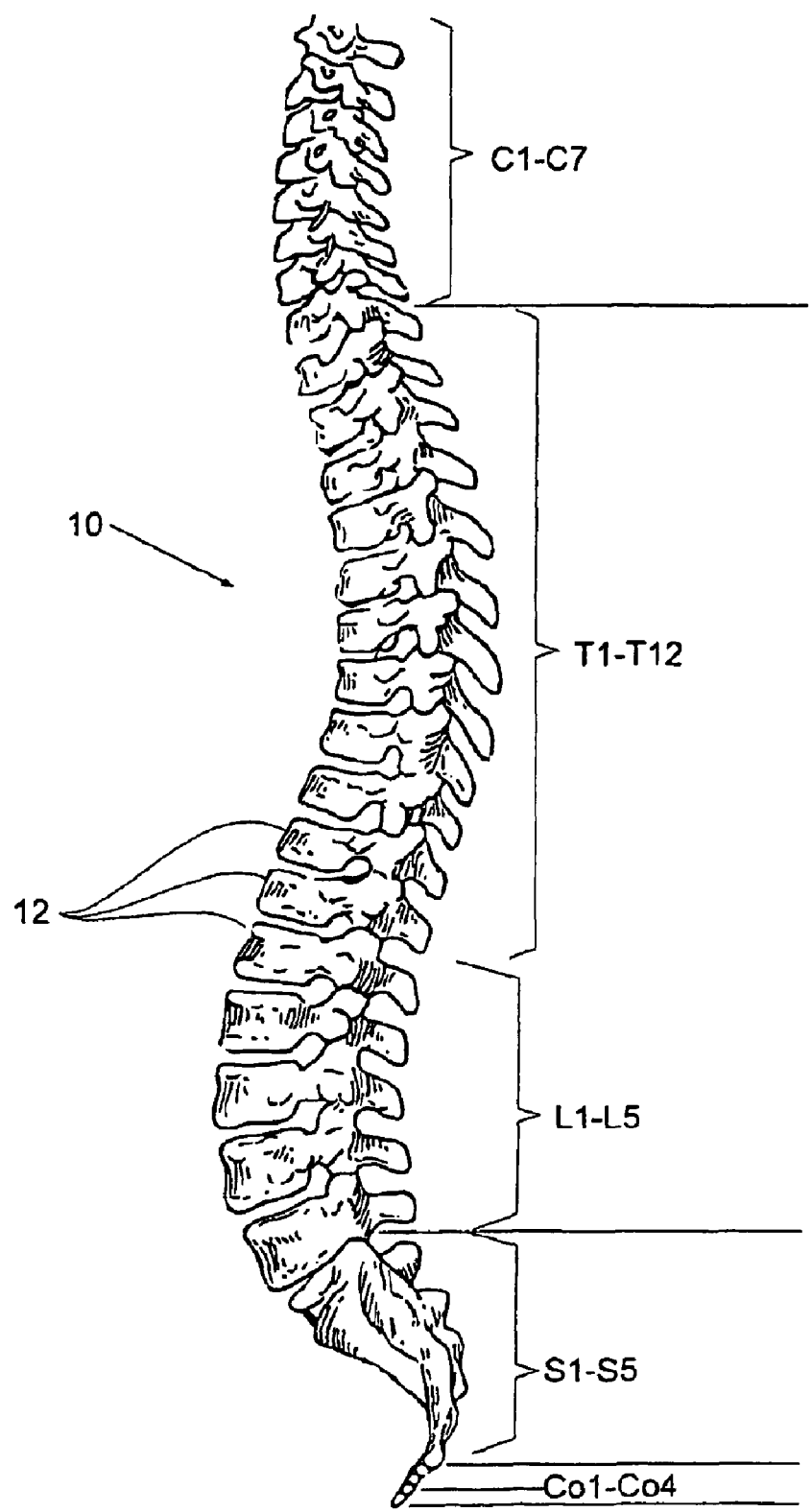
FIG. 1 is a lateral elevation view of a normal human spinal column.
Figure 2:
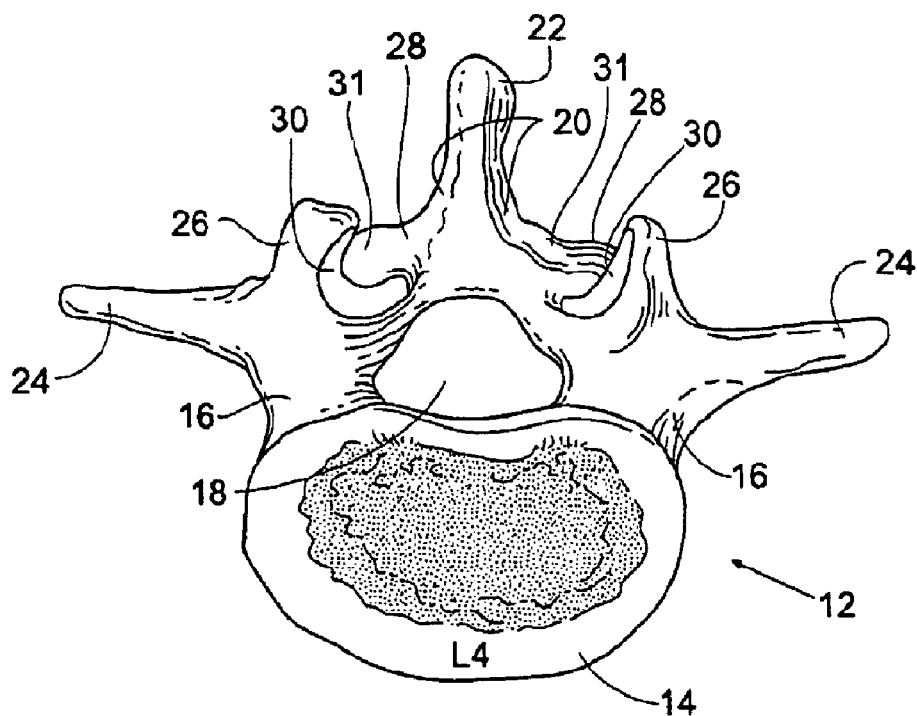
FIG. 2 is a superior view of a normal human lumbar vertebra.
Figure 3:
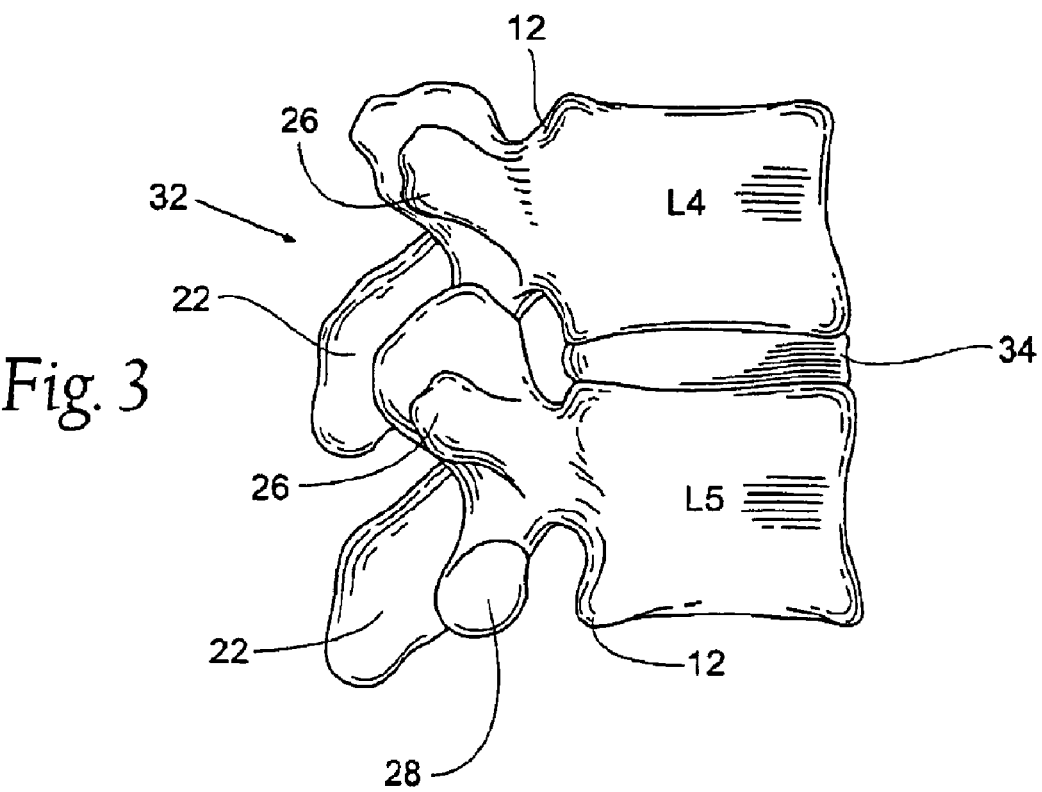
FIG. 3 is a lateral elevation view of a vertebral lumbar facet joint.

FIGS. 4 and 5 illustrate prostheses for replacing the superior and inferior portions of natural facet joints 32 (See also FIG. 3). The prostheses are desirably fixed to vertebral bodies 14 following the surgical removal of the respective natural facet joint portions from the vertebral bodies 14.

The cephalad 36 prosthesis is sized and configured for replacement of the natural inferior facet of a facet joint 32 following removal of the natural inferior facet of the facet joint 32. The caudal prostheses 38 are sized and configured for replacement of the natural superior facet of a facet joint 32 following removal of the natural superior facet of the facet joint 32.

Figure 11:
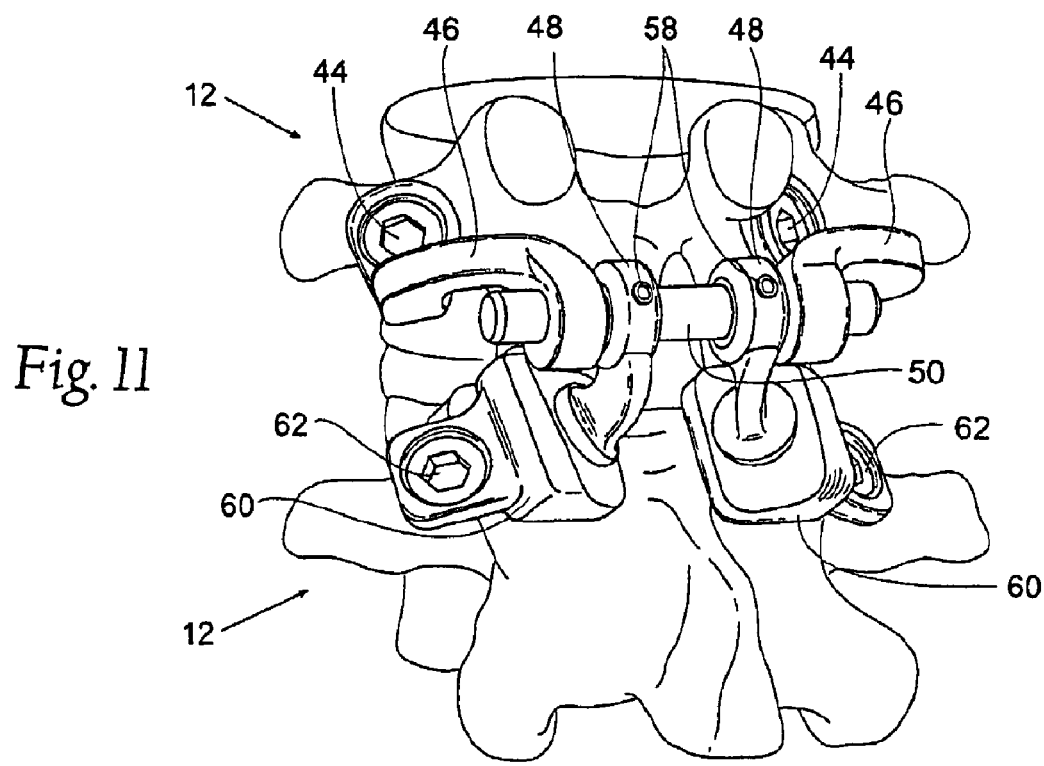
FIG. 11 is a posterior perspective view of the lumbar vertebrae shown in FIG. 10, illustrating the fixation of the cephalad artificial facet joint structures in an articulating configuration with the caudal artificial facet joint structures.

As best shown in FIG. 11, the prostheses 36 and 38 are desirably used in articulated association between a given pair of vertebral bodies 14. As FIG. 11 shows, the caudal and cephalad prostheses 36 and 38 form an articulated system that permits total (superior and inferior) facet joint replacement of one or more natural facet joints 32. The system can provide a succession of entirely artificial facet joint structures between two vertebral bodies 14 or along a length of the spinal column 10.

A. The Cephalad Prosthesis

The cephalad 36 prosthesis shown in FIGS. 4 and 5 is so designated because it provides one or more artificial facet joint structures 40 for repair/replacement of the inferior facet of a natural facet joint 32. The prosthesis 36 allows for the removal of injured, diseased and/or deteriorating natural inferior articular surfaces 28 and supporting bony structure on the vertebra 12 above the facet joint 32. The artificial structures 40 serve to replace the natural inferior processes 28 and supporting bone of the vertebral body 14, which have been desirably removed prior to mounting the prosthesis 36 on the vertebral body 14, as will be described in greater detail later.

The artificial facet joint structures 40 articulate with the superior facet of the facet joint 32. The superior facet can comprise the natural superior portions of the facet joint 32 (i.e., the natural superior articular surfaces 26 and supporting bony structure on the vertebral body 14 below the facet joint 32). Desirably, however, the superior facet comprises an artificial facet joint structure 42 formed by a caudal joint replacement prosthesis 38.

The cephalad prosthesis 36 is a modular unit comprising a pair of fixation elements 44 (left and right), a pair of supports 46 (left and right), a pair of arms 48 (left and right), and a brace 50. The modular unit allows assembly of the components in situ on a vertebra. The cephalad prosthesis 36 may be formed of a material commonly used in the prosthetic arts including, but not limited to, polyethylene, rubber, titanium, chrome cobalt, surgical steel, bony in-growth sintering, sintered glass, artificial bone, ceramics, or a combination thereof.

The left and right fixation elements 44 are fixed to the left and right pedicles 16 respectively, in a position that desirably best assures their fixation to cortical and/or cancellous bone. In the illustrated embodiment, the fixation elements 44 take the form of pedicle screws or nails. The fixation elements 44 are adapted to extend into the right and left pedicles 16 of the vertebral body and serve to anchor the prosthesis 36 in place in an orientation that best assures a secure and durable attachment to bone.

The supports 46 each carry at least one opening 52 sized and configured to accommodate passage of a fixation element 44 to permit mounting of a support 46 on the fixation element 44. The supports 46 are thereby placed on the vertebra 12 in a position dictated by the placement and orientation of the fixation elements 44.

The supports 46 also each have an opening 54 to permit passage of the brace 50. In the illustrated embodiment, the brace 50 takes the form of a transverse rod. Similar to the 46 supports, the left and right cephalad arms 48 have openings 56 to permit passage of the brace 50. The brace 50 is sized to extend across the laminae 20 of a vertebral body 14 and passes through the support openings 54 and the arm openings 56 to hold the supports 46 and arms 48 to thereby stabilize the prosthesis 36.

Each arm 48 carries an artificial facet joint structure 40 for repairing/replacing the inferior facet of a natural facet joint 32. The position of the arms 48 may be adjusted along the brace 50 to bring the artificial facet joint structures 40 of the cephalad prosthesis 36 in articulating configuration with the natural superior facet of the facet joint 32 or an artificial facet joint structure 42 formed by a caudal joint replacement prosthesis 38. The arms 48 can then be secured by locking pins 58 or other suitable mechanism in a desired position.

B. The Caudal Prosthesis

The caudal prostheses 38 shown in FIGS. 4 and 5 are so designated because they create artificial facet joint structures 42 for the superior facet of a natural facet joint 32. The caudal prostheses 38 allow for the removal of injured, diseased and/or deteriorating natural superior articular surfaces 26 and supporting bony structure on the vertebral body 14 below the facet joint 32. The artificial structures 42 serve to replace the natural superior processes 26 and supporting bone of the vertebral body 14, which have been desirably removed prior to mounting the prosthesis 38 on the vertebral body 14. This aspect will be described in greater detail later.

In use, the artificial facet joint structure 42 articulates with the inferior facet of the facet joint 32. The inferior facet can comprise the natural inferior portions of the facet joint 32 (i.e., the natural inferior articular surfaces 28 and supporting bony structure on the vertebral body 14 above the facet joint 32). Desirably, however, the inferior facet comprises an artificial facet joint structure 40 formed by a cephalad joint replacement prosthesis 36, as previously described.

Each prosthesis 38 comprises an artificial facet joint structure 42 and a fixation element 62. Desirably, as FIGS. 4 and 5 illustrate, a pair of fixation elements 62 (right and left) and a pair of artificial facet joint structures 42 (right and left) are provided to permit bilateral facet joint replacement. The left and right fixation elements 62 are fixed to the left and right pedicles 16 respectively, in a position that best assures their fixation to cortical and/or cancellous bone. In the illustrated embodiment, the fixation elements 62 take the form of pedicle screws or nails. The fixation elements 62 are adapted to extend into the right and left pedicles 16 of the vertebral body 14 and serve to anchor the prostheses 38 in place in an orientation that best assures a secure and durable attachment to bone.

Each artificial facet joint structure 42 has at least one opening 64 sized and configured to accommodate passage of a fixation element 62 to permit mounting of the artificial facet joint structure 42 on a fixation element 62. The artificial facet joint structures 42 are thereby placed on the vertebra 12 in a position dictated by the placement and orientation of the fixation elements 62.

The artificial facet joint structures 42 articulate with the natural inferior facet portion of the facet joint 32 or an artificial facet joint structure 40 formed by a cephalad joint replacement prosthesis 36, as previously described.

The caudal prostheses 38 may be formed of a material commonly used in the prosthetic arts including, but not limited to, polyethylene, rubber, titanium, chrome cobalt, surgical steel, bony in-growth sintering, sintered glass, artificial bone, ceramics, or a combination thereof.

C. Artificial Facet Structure Configuration

In the prostheses 36 and 38, each artificial facet joint structure 40 and 42 creates a bearing surface having a configuration that facilitates articulation with the bearing surface of another artificial facet joint structure 40 or 42. The particular geometry for the bearing surface configuration for a given artificial facet joint structure 40 and 42 can vary. It can, for example, be concave, convex, or flat. It may also include a hybrid of curved and flat bearing surface designs, i.e., Miniscal, hinge, etc.

The radii of two articulating bearing surface configurations are desirably selected and matched, taking into account the material from which the surfaces are formed, to minimize contact stress during articulation. The features of the two bearing surfaces (as well as the various other features of the facet joint structures) may also be chosen, if desired, to duplicate the natural articulation of the natural facet joint. Alternatively, the features of the two bearing surfaces (as well as the various other features of the facet joint structures) can be chosen to permit the treated motion segment to experience a lesser or greater degree of articulation than that allowed by the natural motion segment.

For example, in the embodiment illustrated in FIG. 4, the cephalad prosthesis 36 includes artificial facet structures 40 employing generally convex surfaces 66, forming hemisphere-like artificial facet joint structures. In this arrangement, the caudal prostheses 38 include artificial facet structures 42 employing generally complementary concave surfaces 68, forming socket-like artificial facet joint structures that articulate with the hemisphere-like artificial facet joint structures. It should be appreciated that the articulating surfaces 40 and 42 can be reversed, with the artificial facet structures 40 of the cephalad prosthesis 36 employing generally socket-like surfaces, and the artificial facet structures 42 of the caudal prostheses 38 employing generally hemisphere-like surfaces.

Alternatively, a Miniscal bearing design could be employed, utilizing a conformal curved surface as one artificial facet joint structure 40 or 42, with the bearing side of the opposed artificial facet joint structure 40 or 42 having an essentially flat surface. A hemiarthroplasty design could also alternatively be employed, in which one surface of the opposing surfaces does not incorporate the use of an artificial facet joint structure 40 or 42.

In another arrangement, one surface of an artificial facet joint structure 40 or 42 can have bearing articulation on both sides of the component and have opposing articulation with a receiving artificial facet joint structure 40 or 42 having opposing mating bearing surfaces.

A variety of materials are suitable for the artificial facet joint structures. 40 and 42. Ceramic or ceramic in opposition with a chrome alloy can be used. Suitable stainless steel, including 3161, or titanium alloys, with or without the use of surface hardening and overlay, or hard surface coatings, including zirconia and alumina, can also be employed. The metal surfaces can be made from cast, wrought, hot-forged, or powder-metal consolidated sintered materials. Any of these metals or combination of metals and ceramics can be used in articulation with each other. Biocompatible polymers, e.g., polyethylene, can also be used in articulation with the metals, ceramic, and surface-hardened metals just described. Ultra High Molecular Weight Polyethylene can further be gamma-irradiated, as-molded or as-machined.

The radii of articulating artificial facet joint structures 40 and 42 are desirably closely matched to provide contact stress values less than a given threshold value. The desired contact stress value changes with the material employed.

For example, the contact stress value for metal-to-metal bearing combinations is desirably less than about 25,000 psi, and preferably less than 12,000 psi. For polymer surfaces bearing against a metal, ceramic, or surface-hardened metal counter bearing surface, the contact stress value is desirably less than 10,000 psi, and preferably less than 5,000 psi.

For a given material to achieve a desired contact stress value less than the threshold value, the appropriate radii is desirably chosen. Thus, the desired radii may change as material changes.

D. Total Facet Replacement Using the Cephalad and Caudal Prostheses

Figure 6:
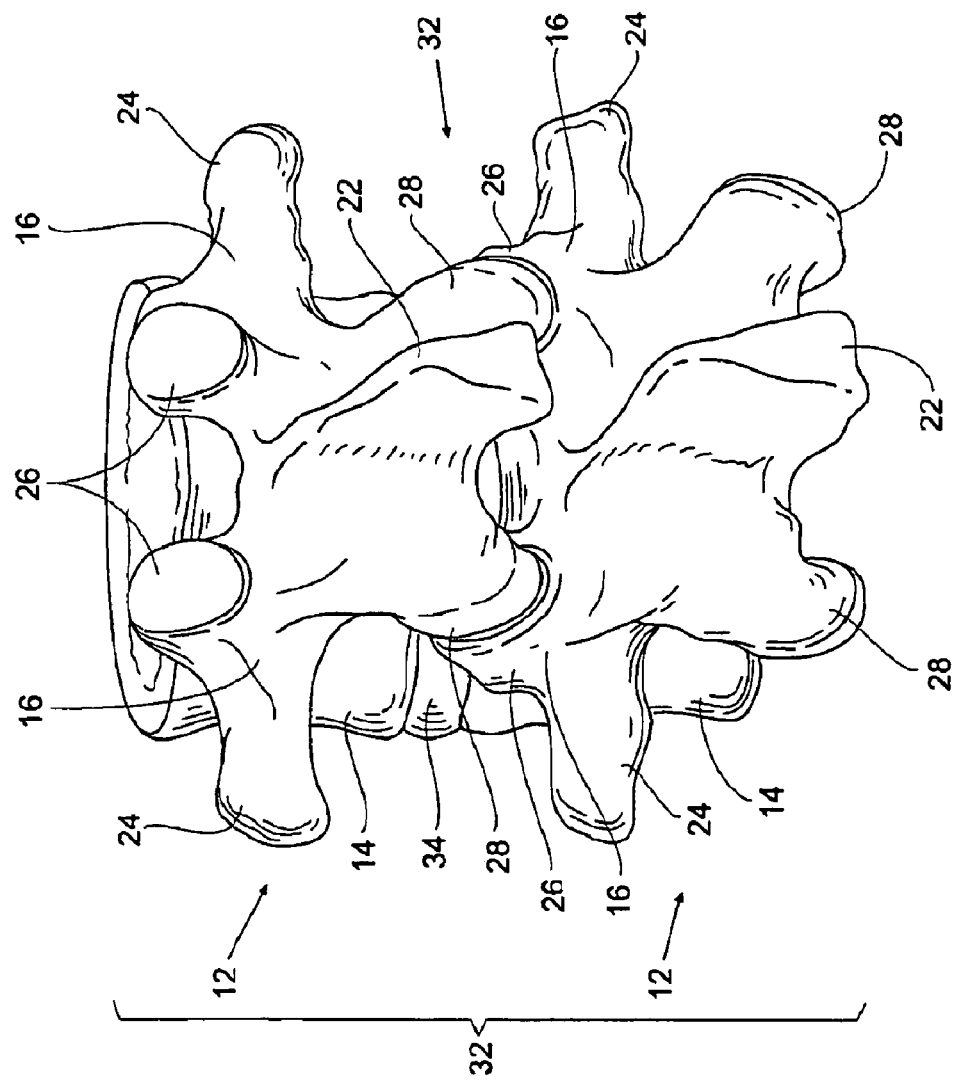
FIG. 6 is a posterior perspective view of the natural left and right facet joints between two lumbar vertebrae.

FIG. 6 shows a normal natural human vertebral facet joint 32, e.g., L4-L5. In some cases of disease or trauma, it may be desirable to remove the superior and inferior facets of the natural facet joint 32 and replace them respectively with the caudal prostheses 38 and the cephalad prosthesis 36.

Figure 7:
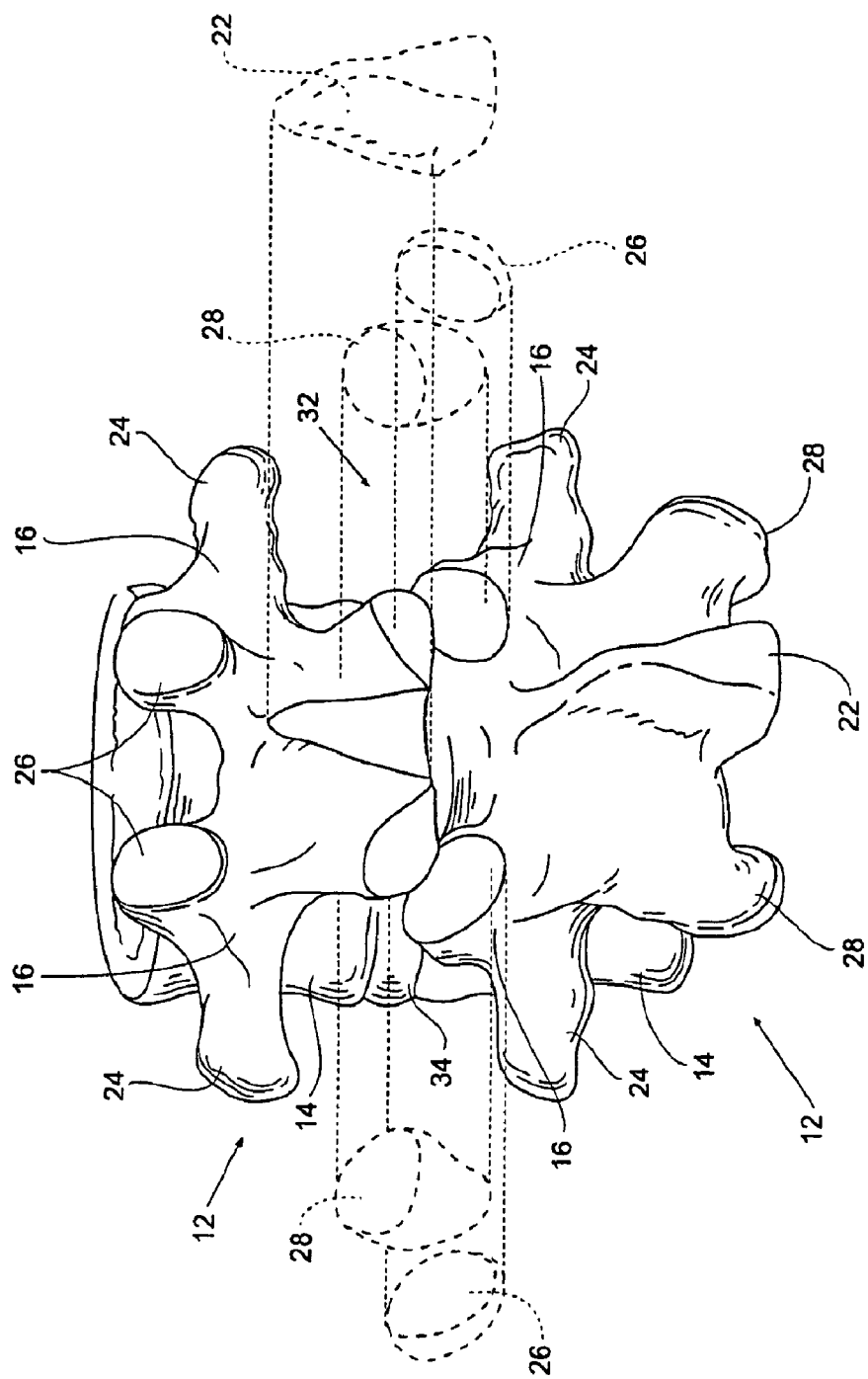
FIG. 7 is a posterior perspective view of the lumbar vertebrae shown in FIG. 6, showing one embodiment of a surgical removal of the spinous process and natural inferior processes and related bony structure of the superior vertebra and the surgical removal of the natural superior processes and related bony structure of the inferior vertebra.

FIGS. 6 and 7 show the exposed spinous process 22, lamina 20, and facet joint 32 of the L4-L5 joint. In this embodiment, a portion of the inferior lamina 20 and the inferior facet of the natural facet joint 32 (e.g., the articulated inferior processes 28 and its supporting bone of the vertebral body 14 above the facet joint 32) are removed. The lamina 20 is cut for a wide decompressive laminectomy along a decompressive superior-to-inferior resection line on both sides of the vertebral body 14. The removed natural anatomy is replaced with the cephalad prosthesis 36. The superior facet of the natural facet joint 32 (e.g., the articulated superior process 26 and its supporting bone of the targeted vertebral body 14) is also removed. Desirably, the mamillary process, the accessory process, a portion of the transverse process, and a portion of the pedicle is removed by being rongeured or reamed. The removed natural anatomy is replaced with the caudal prosthesis 38. The cephalad prosthesis 36, as described above, can be installed over the lamina 20, either before or after placement of the caudal prosthesis 38.

As best shown in reference to FIG. 7, the embodiment of a surgical procedure exposes the spinous process 22, lamina 20, and facet joints 32 at a desired level of the spine 10 using any method common to those of skill in the medical arts.

A portion of the spinous process 22 of the superior vertebra 12 is desirably removed, as depicted by phantom lines in FIG. 7, using any means common in the field. The inferior facet of the facet joint 32 is cut at or near a selected resection line. Most of the lamina 20 is desirably preserved, as is the facet joint capsule, which may be opened and folded back. The facet joint capsule may be cut perpendicular to its direction. The natural inferior facet of the facet joint 32 may then be retracted from the superior facet. Once the inferior and superior facets of the facet joint are separated, the cut inferior bone, e.g., the inferior articular process 28 and its supporting bone, of the upper half of the joint (e.g., the cut inferior portion of the L4 vertebra in the L4-L5 joint) may be removed, as also depicted by phantom lines in FIG. 7. Alternatively, it may be possible to remove the cut inferior bone while simultaneously separating the facet joint 32.

Prominent bone of the superior facet of the natural facet joint 32, e.g., the superior articular process 26 and its supporting bone, may be also removed, as also depicted by phantom lines in FIG. 7, using any means common in the field. The superior facet of the natural facet joint 32 may also be trimmed to decompress the adjacent nerve root. A reamer or any other instrument that is useful for grinding or scraping bone, may be used to ream the superior facet of the facet joint 32 into the pedicle 16, to reach the geometry shown in FIG. 8, which is desirably suitable for receiving the caudal prosthesis 38.

Figure 8:
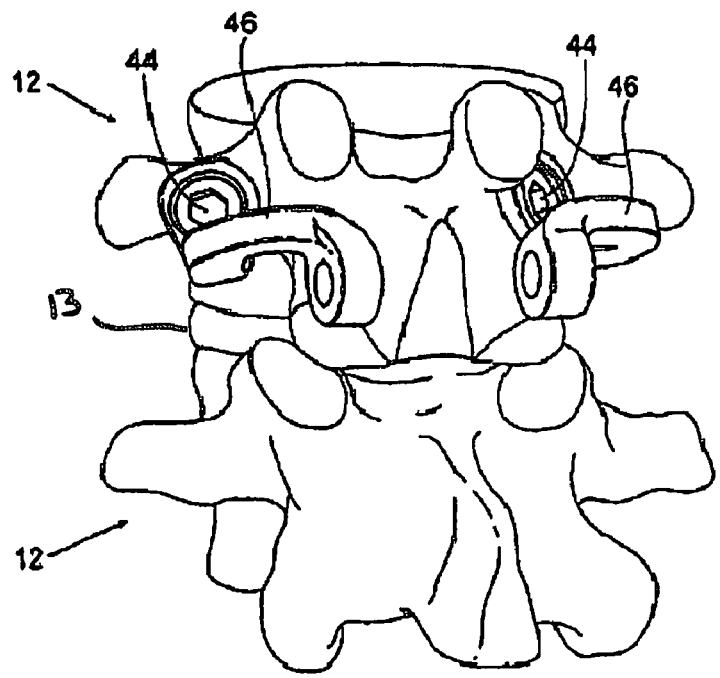
FIG. 8 is a posterior perspective view of the lumbar vertebrae shown in FIGS. 6 and 7, after removal of the inferior and superior halves of the natural facet joints, illustrating the mounting of the left and right support components of the cephalad prosthesis for replacing the inferior halves of the natural facet joints that have been removed onto fixation elements secured within the superior vertebra.

With reference to FIG. 8, a cephalad support 46 is mounted on each of the cephalad fixation elements 44 and the fixation elements 44 are then placed in a desired position on the pedicles 16 (with one fixation element 44 on each of the right and left pedicles 16) and screwed securely into the superior vertebral body 14.

Figure 9:
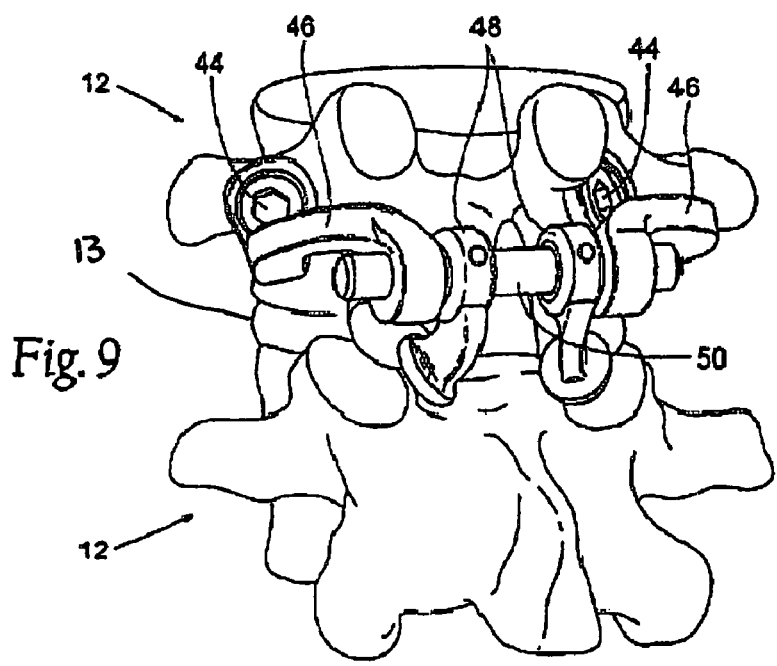
FIG. 9 is a posterior perspective view of the lumbar vertebrae shown in FIG. 8, illustrating the placement of the transverse rod and left and right cephalad arm components of the cephalad prosthesis onto the superior vertebra for replacing the inferior halves of the natural facet joints that have been removed.

As FIG. 9 illustrates, the cephalad arms 48 are then placed medial to the left and right supports 46. The brace 50 is then passed through the openings 54 and 56 of the supports 46 and arms 48.

Figure 10:
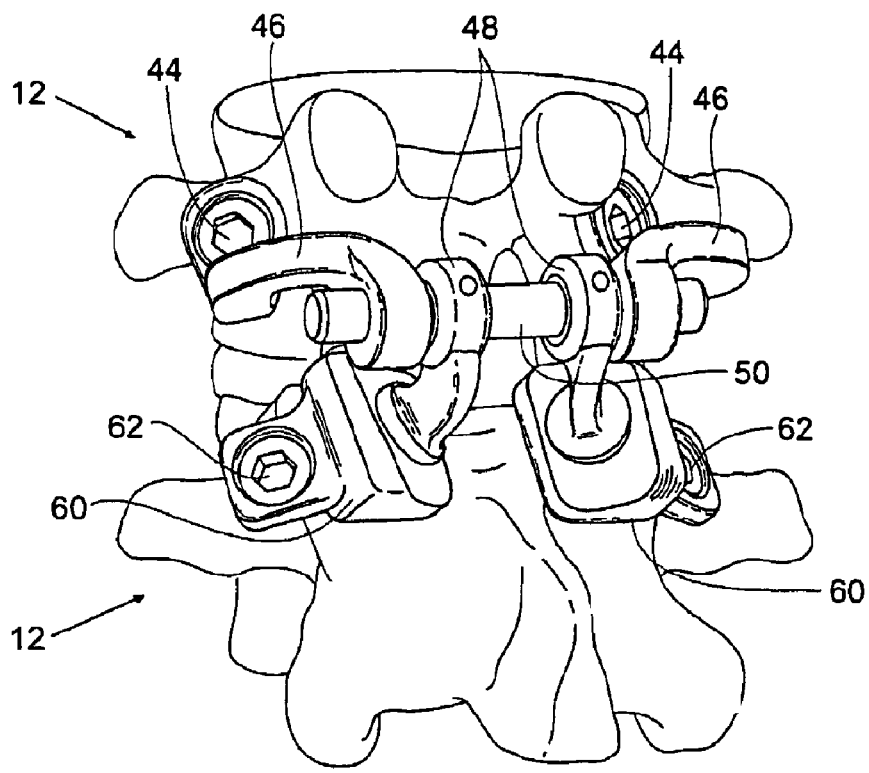
FIG. 10 is a posterior perspective view of the lumbar vertebrae shown in FIG. 9, illustrating the mounting of caudal prostheses for replacing the superior halves of the natural facet joint that have been removed onto fixation elements secured within the inferior vertebra.

The caudal artificial facet joint structures 42 are then mounted on the caudal fixation elements 62 and the fixation elements 62 are then placed in a desired position on the pedicles 16 (with one fixation element 62 on each of the right and left pedicles 16) and screwed securely into the inferior vertebral body, as shown in FIG. 10.

With reference to FIG. 11, the cephalad arms 48 are then positioned to bring the artificial facet joint structures 40 of the cephalad prosthesis 36 in articulating configuration with the artificial facet joint structures 42 of the caudal prosthesis 38. The arms 48 are then secured in the desired position by use of locking screws 58 or other suitable mechanism.

Further details of surgical procedures suitable for installing the prostheses are described in co-pending U.S. patent application Ser. No. 09/693,272, filed Oct. 20, 2000, and entitled "Facet Arthroplasty Devices and Methods," which has issued into U.S. Pat. No. 6,610,091, and which is incorporated herein by reference.

II. First Alternative Embodiment

A. Cephalad Prosthesis

Figure 12:
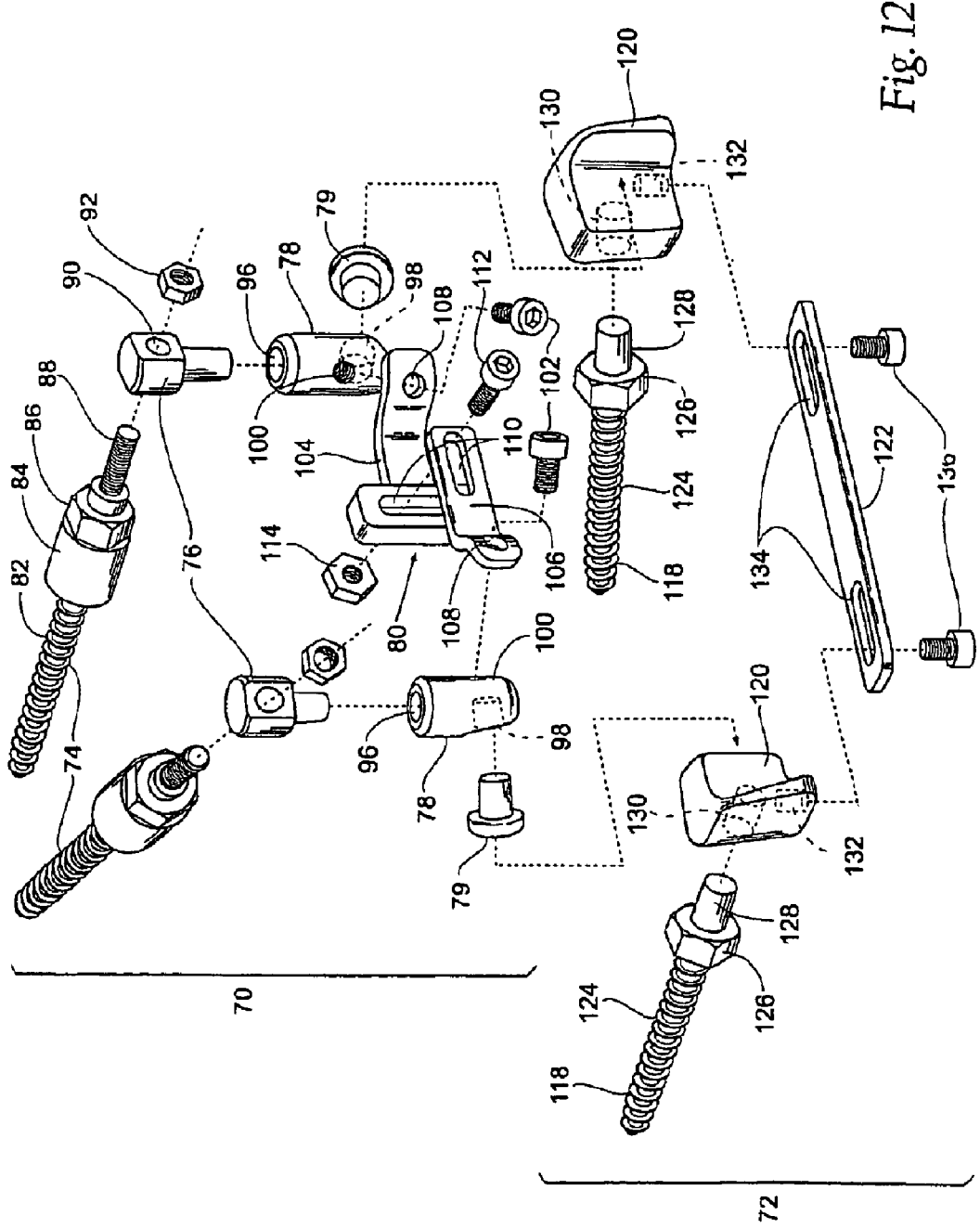
FIG. 12 is an exploded perspective view of an alternative embodiment of cephalad and caudal prostheses for replacing, respectively, the inferior and superior halves of a natural facet joint.
Figure 13:
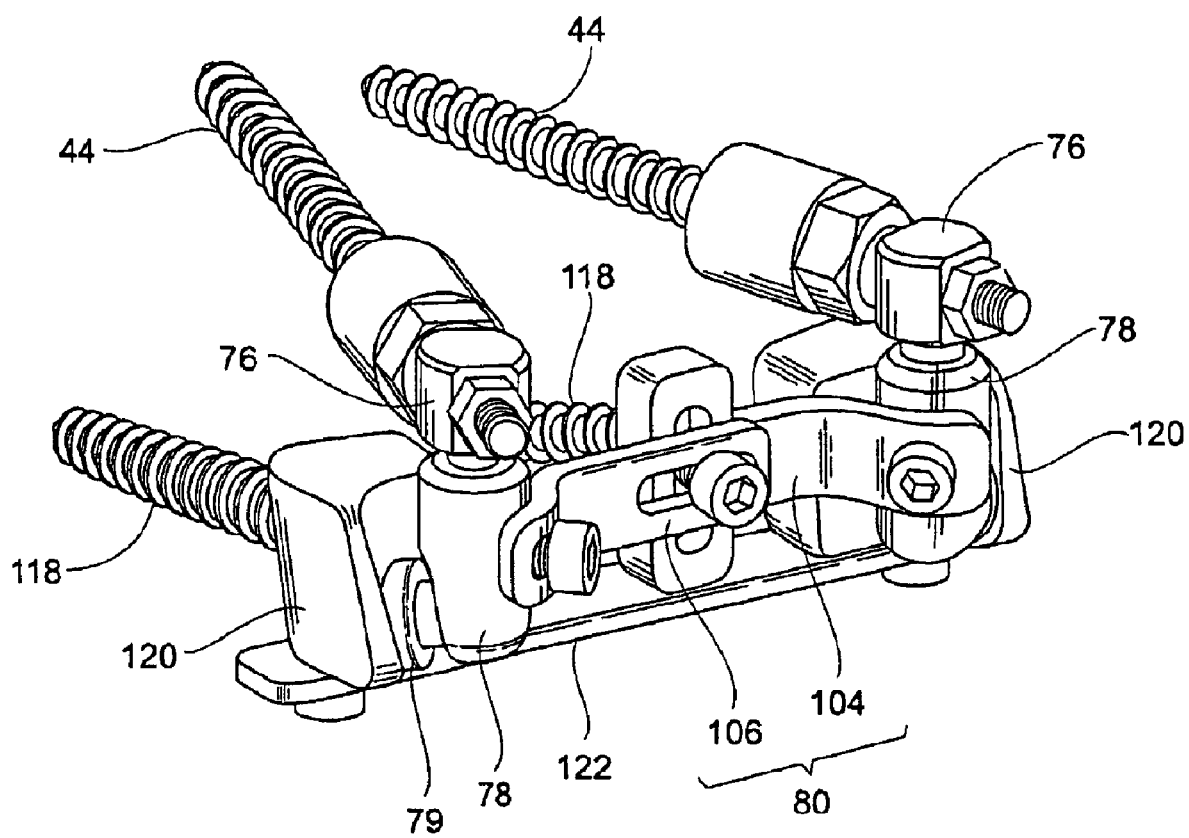
FIG. 13 is an assembled perspective view of the prostheses shown in FIG. 12.

FIGS. 12 and 13 show alternative embodiments of a cephalad 70 and a caudal 72 vertebral prosthesis. Similar to the previous embodiment, the cephalad prosthesis 70 is a modular unit comprising left and right fixation elements 74, left and right supports 76, left and right arms 78, left and right artificial facet joint structures 79 for the superior facet of a natural facet joint 32, and a transverse brace 80 that allows assembly of the components in situ. Components are mounted in situ on the fixation elements 74 that are secured to the pedicle 16 in an orientation that provides secure fixation to bone.

The left and right fixation elements 74 are fixed to the left and right pedicles 16 respectively, in a position that best assures their fixation to cortical and/or cancellous bone. In the illustrated embodiment, the fixation elements 74 take the form of pedicle screws or nails. The fixation elements 74 are adapted to extend into the right and left pedicles 16 of the vertebral body 14 and serve to anchor the prosthesis 70 in place in an orientation that best assures a secure and durable attachment to bone.

The fixation elements 74 have a threaded body 82 configured to screw into the pedicle 16. A spacing collar 84 may be provided to add additional length to the fixation element 74 if necessary to assure its fixation in the vertebra 12. A nut 86 may be provided to couple with a wrench or other tool to facilitate screwing the fixation element 74 into the vertebra 12. An end portion 88 passes through an opening 90 in the support 76 and permits attachment of the support 76 to be secured by nut 92 or other fixation means, e.g., by threaded engagement.

Figure 19:
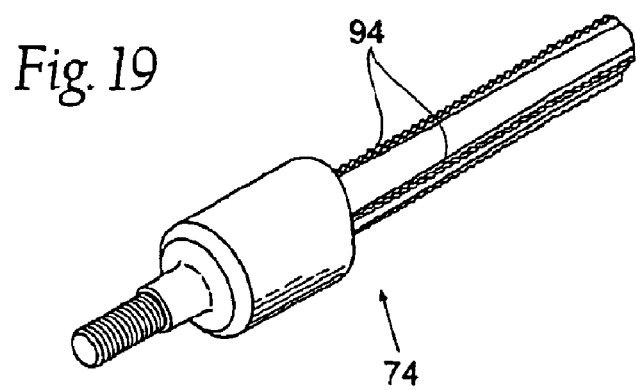
FIG. 19 is a perspective view of an alternative embodiment of the cephalad prosthesis fixation element shown in FIG. 1, illustrating the body of the fixation element being of a stem configuration.

FIG. 19 shows an alternative embodiment of a fixation element 74 in which the body 82 is a stem configuration. In this arrangement, the fixation element 74 is placed into a hole that has been reamed into the bone and secured by adhesive or boney in-growth material. The stem may include a series of serrated vanes 94 to prevent rotation in bone.

With reference back to FIG. 12, in the illustrated embodiment, the support 76 takes the form of a right angle connector. The support 76 is sized and configured to couple with the arm 78, e.g., by Morse taper. The arm 78 is a generally cylindrical member having a first bore 96 configured, e.g., tapered, to receive the support 76. A second bore 98 permits the arm 78 to couple with an artificial facet joint structure 78 for repairing/replacing the inferior facet of a natural facet joint 32, e.g., the bore 98 may be tapered to couple with the artificial facet joint structure 78 by Morse taper. A third bore 100 receives a fixation element 102, e.g., screw, to secure the arm 78 to brace 80.

The transverse brace 80 comprises a right component 104 and a left component 106. An end opening 108 in each of the components 104 and 106 receives a fixation element 102 to fix the right and left components 104 and 106 to the right and left arms 78 respectively, e.g., by threaded engagement. Each component 104 and 106 desirably has a medial opening 110. The medial openings 110 are sized and configured to overlap and permit passage of a fixation element 112, which may be secured by nut 114 or similar mechanism, to thereby couple the components 104 and 106 together to form the transverse brace 80. Similar to brace 50 described in relation to the previous embodiment, the brace 80 extends across the laminae 20 of a vertebral body 14, providing a width-adjustable load-bearing support that further stabilizes the prosthesis 70.

B. Caudal Prosthesis

With continued reference to FIGS. 12 and 13, the caudal prosthesis 72 is a modular unit comprising left and right fixation elements 118, left and right artificial facet joint structures 120, and a transverse brace 122 that allows assembly of the components in situ. Components are mounted in situ on the fixation elements 118 that are secured to the pedicle 16 in an orientation that provides secure fixation to bone.

The left and right fixation elements 118 are fixed to the left and right pedicles 16 respectively, in a position that best assures their fixation to cortical and/or cancellous bone. In the illustrated embodiment, the fixation elements 118 take the form of pedicle screws or nails. The fixation elements 118 are adapted to extend into the right and left pedicles 16 of the vertebral body 14 and serve to anchor the prosthesis 72 in place in an orientation that best assures a secure and durable attachment to bone.

The fixation elements 118 have a threaded body 124 configured to screw into the pedicle 16. A nut 126 may be provided to couple with a wrench or other tool to facilitate screwing the fixation element 118 into the vertebra 12. An end portion 128 is configured to couple with a support 120, e.g., may be tapered to couple with the support 120 by Morse taper.

Figure 20:
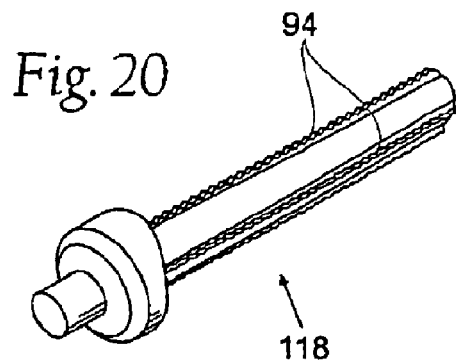
FIG. 20 is a perspective view of another alternative embodiment of the caudal prosthesis fixation element shown in FIG. 1, illustrating the body of the fixation element being of a stem configuration.

FIG. 20 shows an alternative embodiment of a fixation element 118 in which the body 124 is a stem configuration. In this arrangement, the fixation element 118 is placed into a hole that has been reamed into the bone and secured by adhesive or boney in-growth material. The stem may include a series of serrated vanes 94 to prevent rotation in bone.

Turning back to FIGS. 12 and 13, each artificial facet joint structure 120 is sized and configured to be mounted on a fixation element 118, e.g, has a tapered bore 130 to mate with tapered end portion 128 of the fixation element 118. A second bore 132 receives a fixation element 136 to secure the artificial facet joint structure 120 to the caudal brace 122, e.g., by threaded engagement. The artificial facet joint structures 120 articulate with the natural inferior facet portion of the facet joint 32 or an artificial facet joint structure 79 formed by a cephalad joint replacement prosthesis 70, as previously described.

In the illustrated embodiment, the brace 122 takes the form of a transverse bar. The brace 122 desirably has right and left end openings 134 that receive fixation elements 136 for attachment to the right and left supports 122 respectively, e.g., by threaded engagement. The brace 122 extends across the laminae 20 of the inferior vertebra 12 to provide a width-adjustable load-bearing support to further stabilize the caudal prosthesis 72.

C. Total Facet Replacement Using the Cephalad and Caudal Prostheses

In a surgical procedure for total facet replacement using the cephalad and caudal prostheses 70 and 72, the spinous process 22 along with the inferior articular process 28 and its supporting bone, of the upper half of the joint 32 (e.g., the cut inferior facet of the L4 vertebra in the L4-L5 joint) may be removed, as previously described (see FIG. 7). Prominent bone of the superior facet of the natural facet joint 32, e.g., the superior articular process 26 and its supporting bone, may be also removed, as also previously described, using any means common in the field (see FIG. 7).

Figure 14:
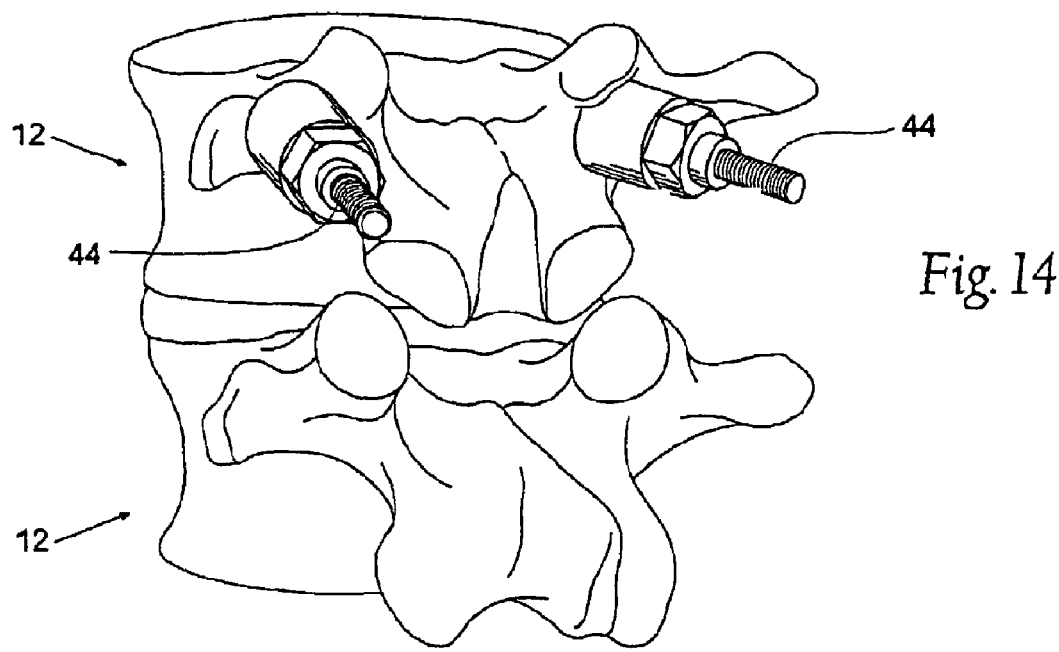
FIG. 14 is a posterior perspective view of the lumbar vertebrae shown in FIGS. 6 and 7, after removal of the inferior and superior halves of the natural facet joints, illustrating the placement of fixation elements of the cephalad prosthesis within the superior vertebra.

As shown in FIG. 14, a cephalad fixation element 74 is placed in a desired position on each of the right and left pedicles 16 of the superior vertebra 12 and secured in the vertebral body 14 by screwing the nut 86.

Figure 15:
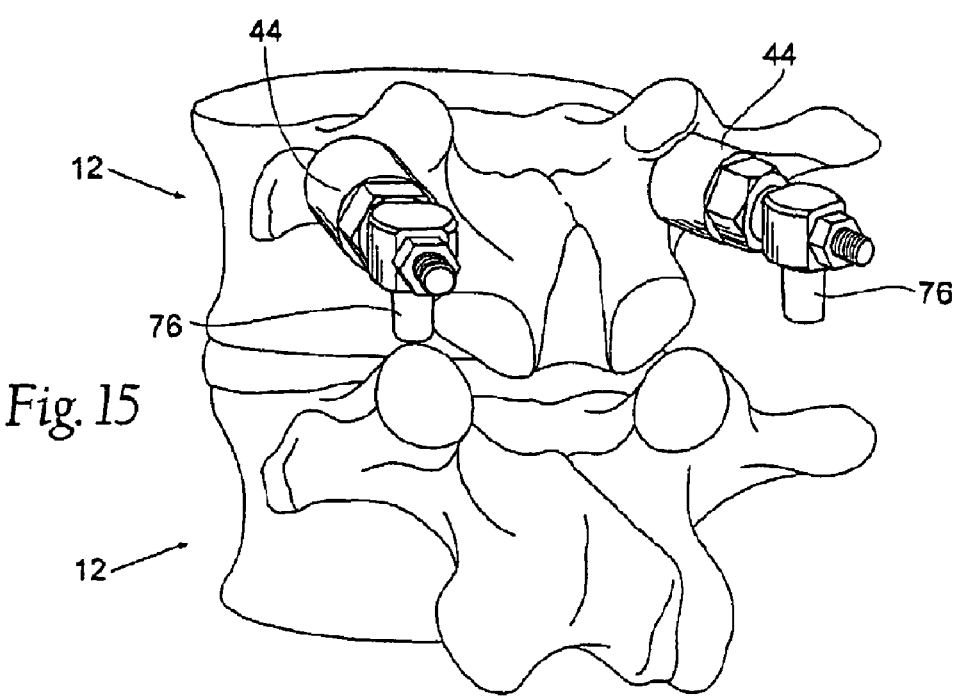
FIG. 15 is a posterior perspective view of the lumbar vertebrae shown in FIG. 14, illustrating the mounting of the left and right cephalad support components of the cephalad prosthesis onto the cephalad fixation elements.
Figure 16:
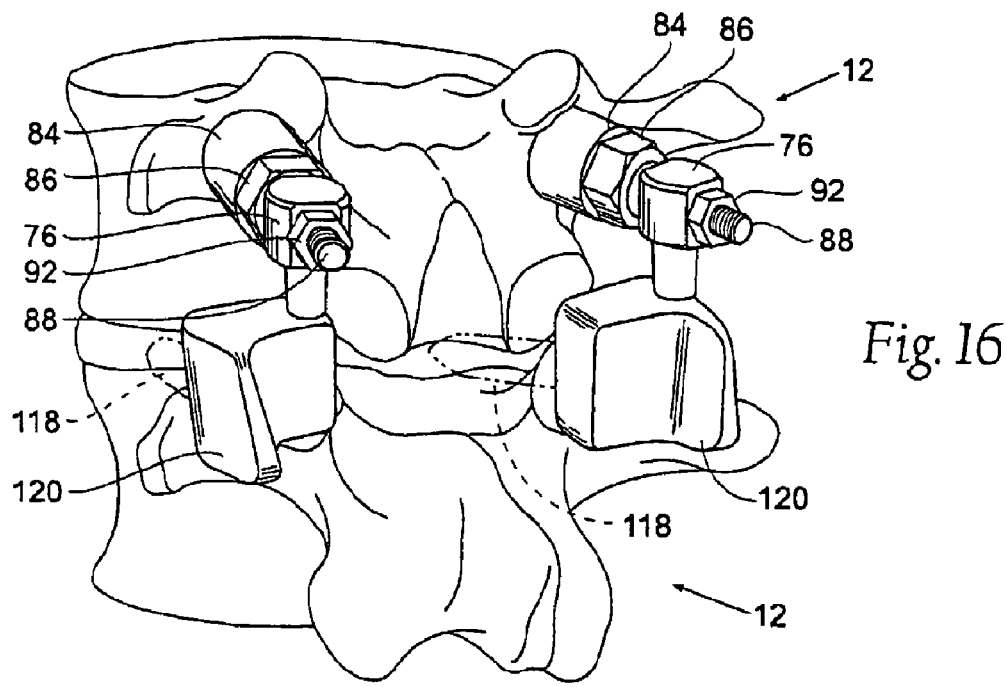
FIG. 16 is a posterior perspective view of the lumbar vertebrae shown in FIG. 15, illustrating the mounting of the left and right caudal support components of the caudal prosthesis onto the caudal fixation elements that have been secured with the inferior vertebra.

A cephalad support 76 is then mounted on each of the fixation elements 74 and secured with a nut 92 or other suitable means, as seen in FIG. 15. With reference to FIG. 16, a caudal fixation element 118 is then placed in a desired position on each of the right and left pedicles 16 of the inferior vertebra 12 and secured in the vertebral body 14 by screwing the nut 126. A caudal support 120 is then mounted on each of the fixation elements 118, as FIG. 16 also shows.

Figure 17:
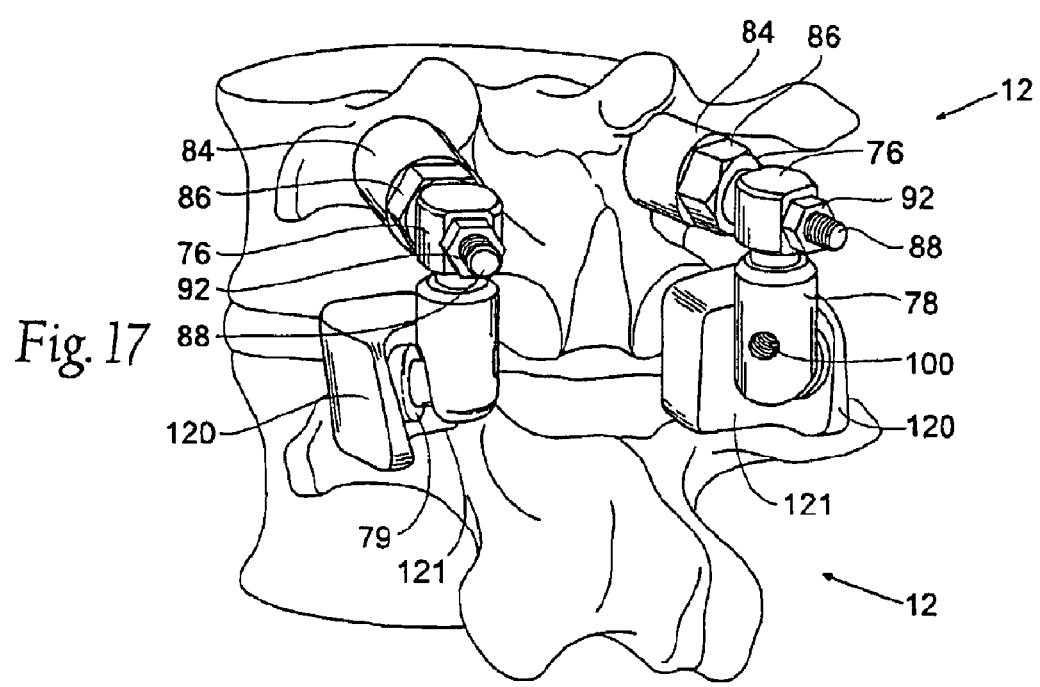
FIG. 17 is a posterior perspective view of the lumbar vertebrae shown in FIG. 16, illustrating the mounting of the arm components of the cephalad prosthesis onto the support components of the cephalad prosthesis.

Referring now to FIG. 17, a cephalad support 76 and a cephalad arm 78 are then mounted on each of the cephalad fixation elements 74. The artificial facet joint structures 79 of cephalad prosthesis 70 are then brought into articulating configuration with artificial facet joint structures 121 of the caudal prosthesis 72 and the arms 78 are secured by nuts 92 or other suitable mechanism.

Figure 18:
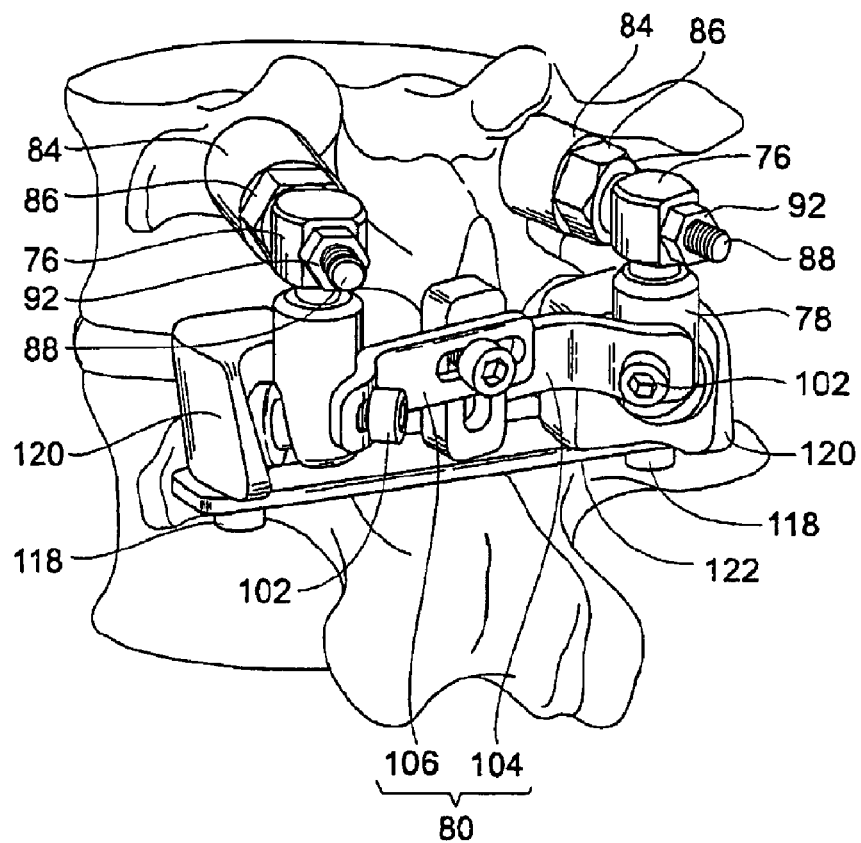
FIG. 18 is a posterior perspective view of the lumbar vertebrae shown in FIG. 14, illustrating the mounting of the left and right cephalad support components of the cephalad prosthesis onto the cephalad fixation elements.

As seen in FIG. 18, the right cephalad brace component 104 is then fixed to the to right cephalad arm 78 and the left cephalad brace component 106 is fixed to left cephalad arm 78 with fixation elements 102 or other suitable mechanism. The left and right brace components 104 and 106 are then secured to each other with a fixation element 112 or other suitable means to form a unitary cephalad transverse brace 80. The caudal supports 120 can then be coupled with the caudal brace 122 using fixation elements 136 or other suitable means.

III. Second Alternative Embodiment

Figure 21:
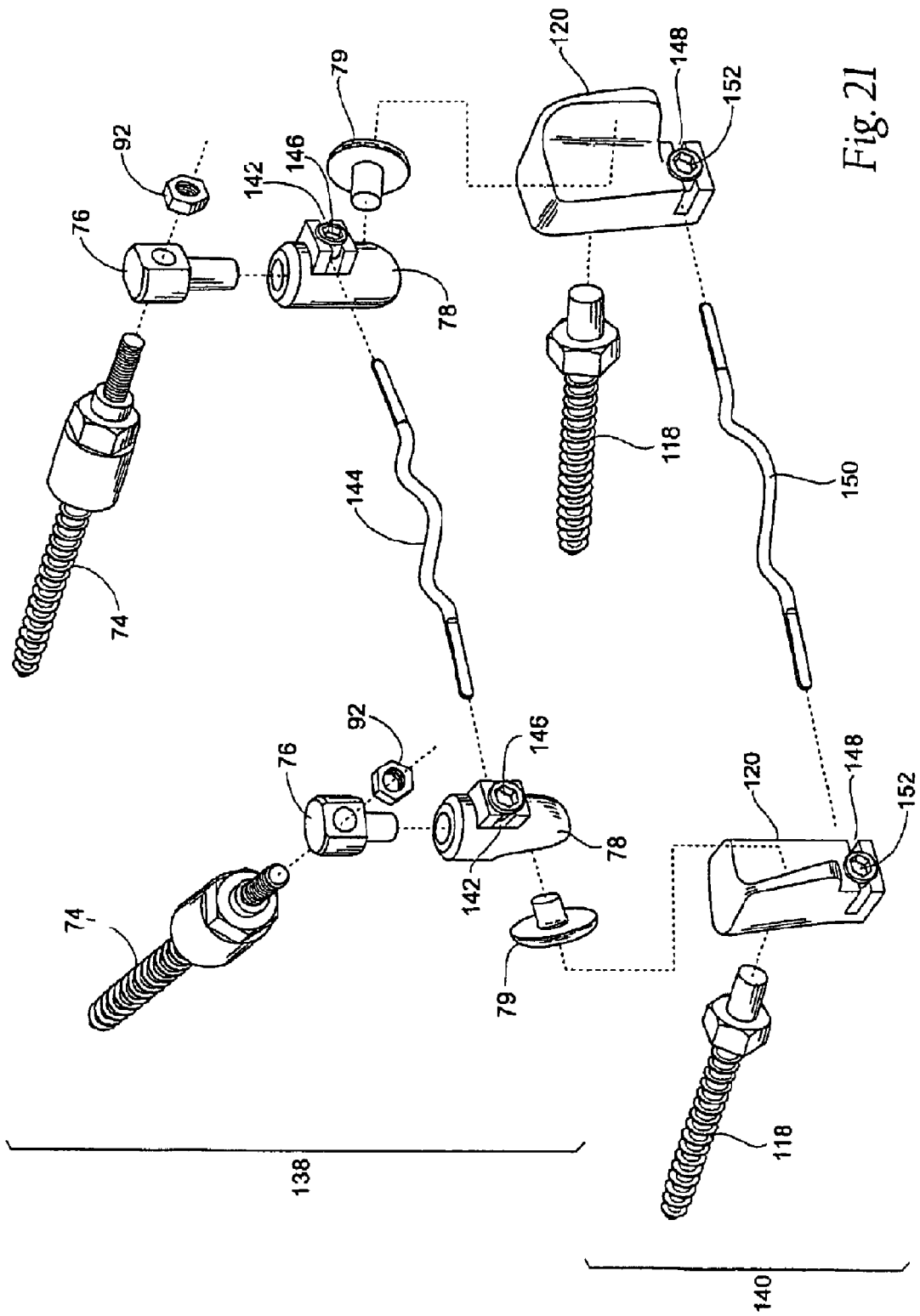
FIG. 21 is an exploded perspective view of an alternative embodiment of cephalad and caudal prostheses for replacing, respectively, the inferior and superior halves of a natural facet joint.
Figure 22:
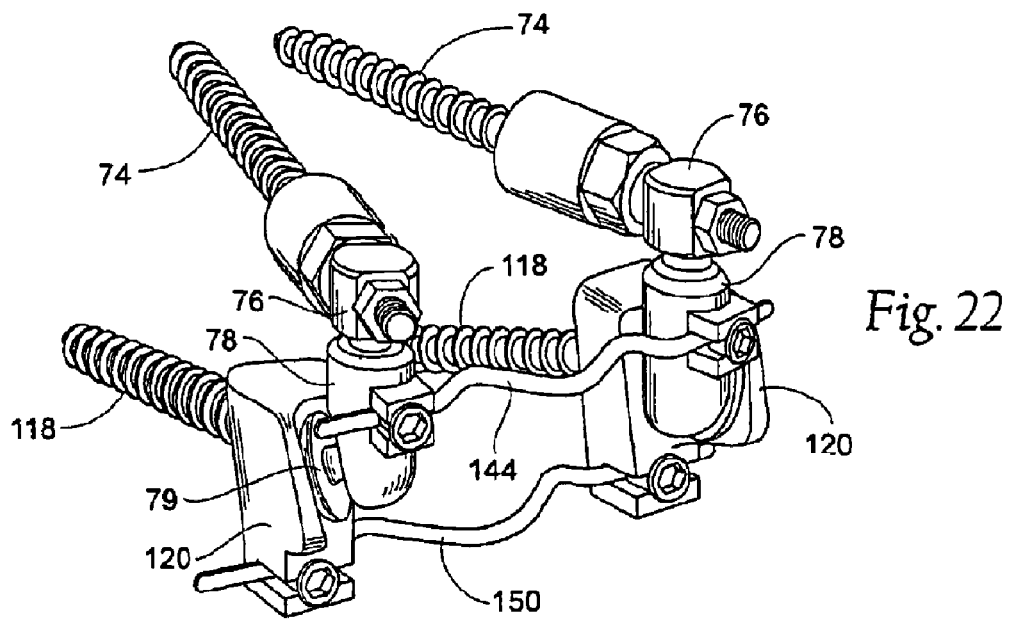
FIG. 22 is an assembled perspective view of the prostheses shown in FIG. 21.
Figure 23:
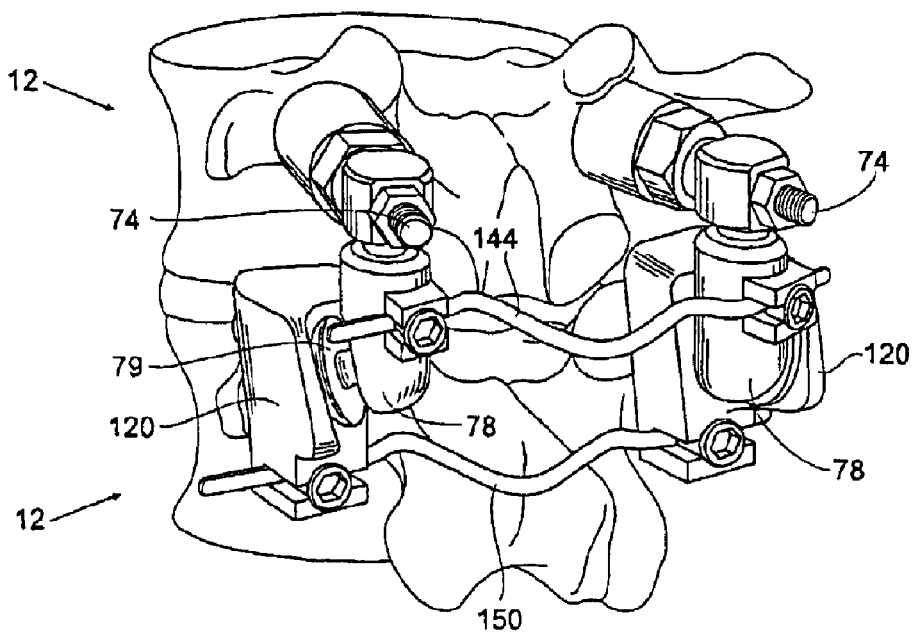
FIG. 23 is a posterior perspective view of the lumbar vertebrae shown in FIGS. 6 and 7, after removal of the inferior and superior halves of the natural facet joints, illustrating the fixation of the cephalad and caudal prostheses shown in FIG. 21 on the vertebrae.
Figure 24:
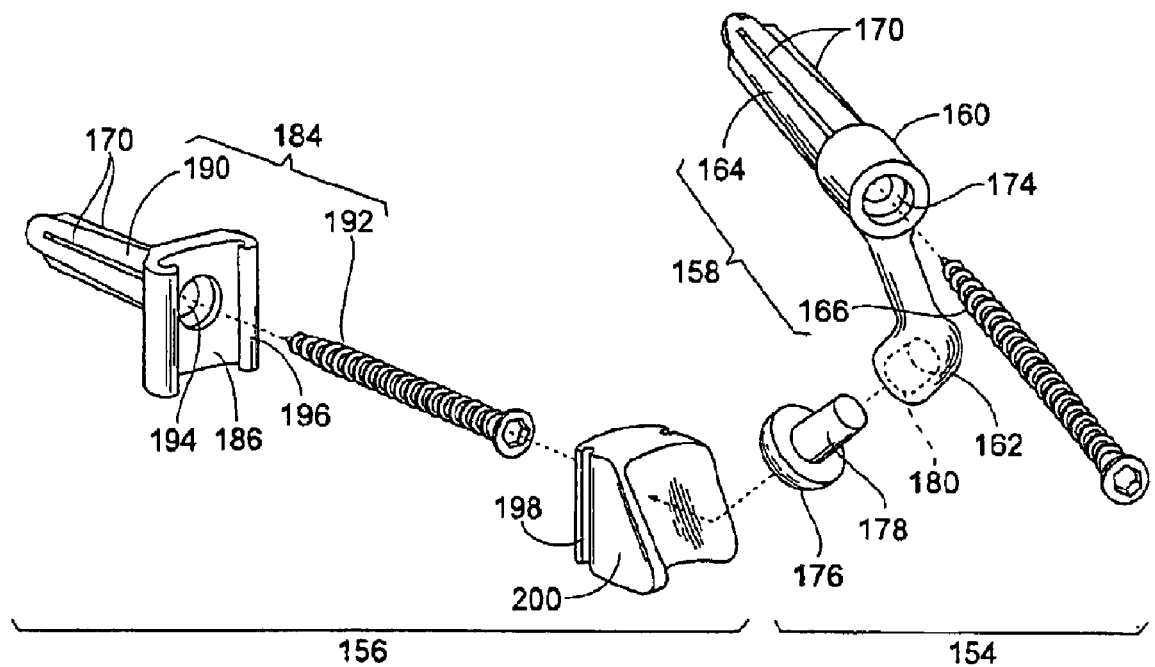
FIG. 24 is an exploded perspective view of an alternative embodiment of cephalad and caudal prostheses for replacing, respectively, the inferior and superior halves of a natural facet joint, illustrating the arm of the cephalad prosthesis including a female fitting and the artificial facet joint structure of the cephalad prosthesis including a complementary male fitting.

FIGS. 21-23 illustrate a cephalad prosthesis 138 and a caudal prosthesis 140 similar to the embodiments shown in FIGS. 12 and 13, and like parts will be given like reference numerals.

Each arm 78 of the cephalad prosthesis 138 includes a slot 142 for receiving a brace 144. In the illustrated embodiment, the brace 144 takes the form of a curvilinear transverse rod. The brace 144 is secured to the arms 78 by fixation elements 146.

Similar to the cephalad prosthesis 138, each support 120 of the caudal prosthesis 140 has a slot 148 for receiving a brace 150. In the illustrated embodiment, the brace 150 takes the form of a curvilinear transverse rod. The brace 150 is secured to the supports 120 by fixation elements 152.

The prostheses 138 and 140 are secured in the vertebrae by surgical procedure, as previously described (see also FIGS. 14-18).

IV. Third Alternative Embodiment

FIGS. 24-28 illustrate another embodiment of a cephalad prosthesis 154 and a caudal prosthesis 156.

A. Cephalad Prosthesis

Similar to the previous embodiments, the cephalad prosthesis 154 is a modular unit comprising a fixation element 158, a support 160, and an arm 162 carrying an artificial facet joint structure 176 that allow assembly of the components in situ. A pair of fixation elements 158 (right and left) are desirably provided and sized and configured to be are secured to the right and left pedicles 16 in an orientation that provides secure fixation to bone. Components are mounted in situ on the fixation elements 158 that are secured to the pedicle 16 in an orientation that provides secure fixation to bone.

In the illustrated embodiment, each fixation element 158 takes the form of a sleeve 164 and a pedicle screw 166. The sleeve 164 is sized and configured for insertion into a bore 168 that has been reamed into the pedicle 16 (see also FIG. 28). The sleeve 164 provides an increased surface area of attachment, further securing the attachment of the prosthesis 154 to bone. Desirably, the sleeve 164 includes a plurality of vanes 170 that resist rotation of the sleeve 164 in bone to further secure the sleeve 164 within the vertebra 12. In one alternative embodiment, the sleeve 164 can comprise an expandable sleeve which expands (in a manner similar to a wall anchor) in diameter (desirably within the bore 168) when the screw 166 is advanced through the sleeve 164.

Figure 39:
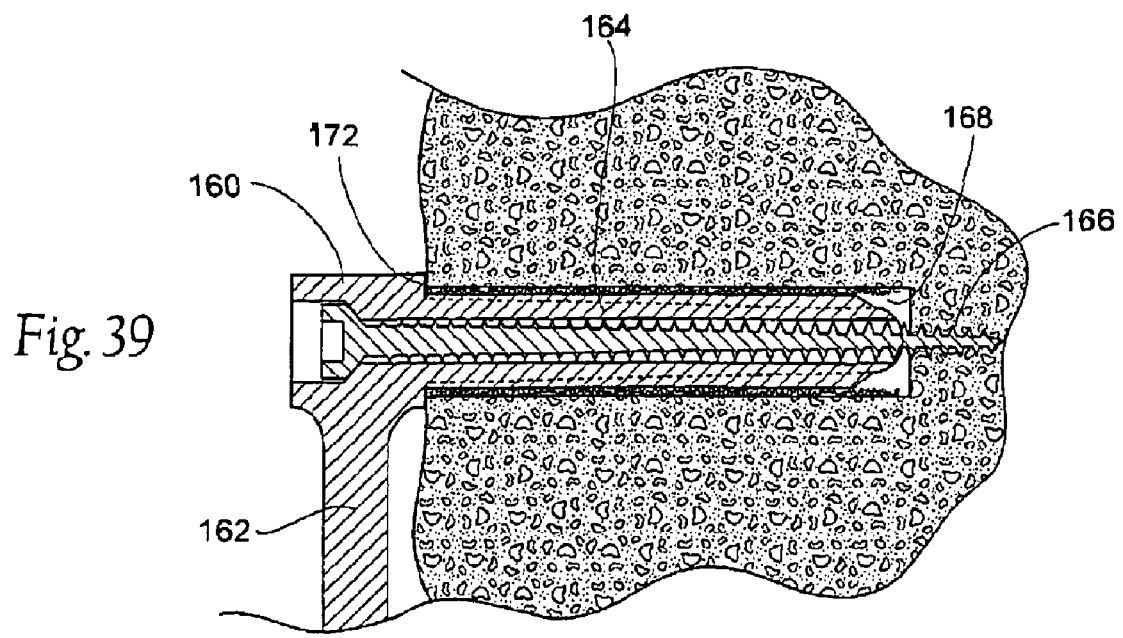
FIG. 39 is a sectional view of a bore within bone, and illustrating the placement of mesh material and a sleeve within the bore.

The sleeve 164 can be secured for long-term fixation within the bore 168 by adhesive, e.g., bone cement. Alternatively, the sleeve 164 could incorporate a boney in-growth outer surface to which the surrounding bone could grow and adhere. Desirably, the sleeve 164 would fit tightly within the bore 168, with the distal section of the screw 166 anchored within the cancellous bone, thereby securely anchoring the sleeve mechanically while allowing the surrounding bone to biologically adhere to the outer surface of the sleeve. As another alternative (as shown in FIG. 39), the sleeve 164 can be secured by boney in-growth with a mesh material 172 placed within the bore 168. The sleeve 164 is then placed within the bore 168, such that it is surrounded by the mesh material 172. The mesh material 172 can be made of titanium, chrome, steel, or other suitable metal alloy for boney in-growth to infiltrate. The pedicle screw 166 provides interim mechanical fixation until the sleeve 164 joins the bone.

A support 160 and arm 162 are integrally formed with the sleeve 164 or otherwise securely mounted on the sleeve 164. An opening 174 in the sleeve 164 extends through the support 160 and serves to receive the pedicle screw 166, e.g., by screwing the pedicle screw 166 into the sleeve 164. The arm 162 is sized and configured to couple with an artificial facet joint structure 176, e.g., by Morse taper or other suitable mechanism that permits rotation (if desired) of the artificial facet joint structure 176 with respect to the support 160 to enable proper orientation of the artificial facet joint structure 176 with the caudal prosthesis 156. In the arrangement illustrated in FIG. 24, the artificial facet joint structure 176 includes a male fitting 178 and the arm 162 includes a complementary female fitting 180. Alternatively, the male fitting 178 and female fitting 180 could comprise a non-circular fitting arrangement (oval, slotted, triangular, polygonal, etc.) that reduces or prevents relative motion between the fittings 178 and 180, but allows the facet joint structure 176 to assume one of two (or more) predetermined positions.

Figure 25:
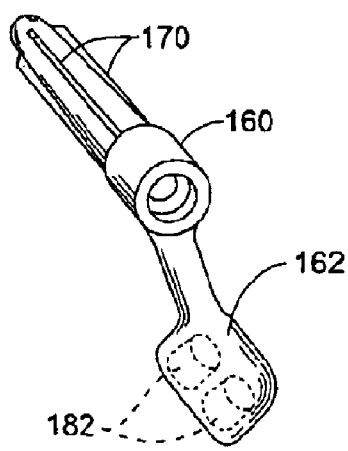
FIG. 25 is an alternative embodiment of the cephalad prosthesis shown in FIG. 24, illustrating multiple attachment sites on the arm for attachment of the artificial facet joint structure.

The arm 162 can be of a fixed length. In a representative embodiment, the arm 162 is approximately 1 cm in length. As FIG. 25 shows, to accommodate individual variations in anatomy and customize the prosthesis 154 to a given individual, the arm 162 may include more than one attachment site 182 for the artificial facet joint structure 176 at different distances along the arm 162. It is contemplated that the number and position of the attachment sites 182 may vary.

Figure 26:
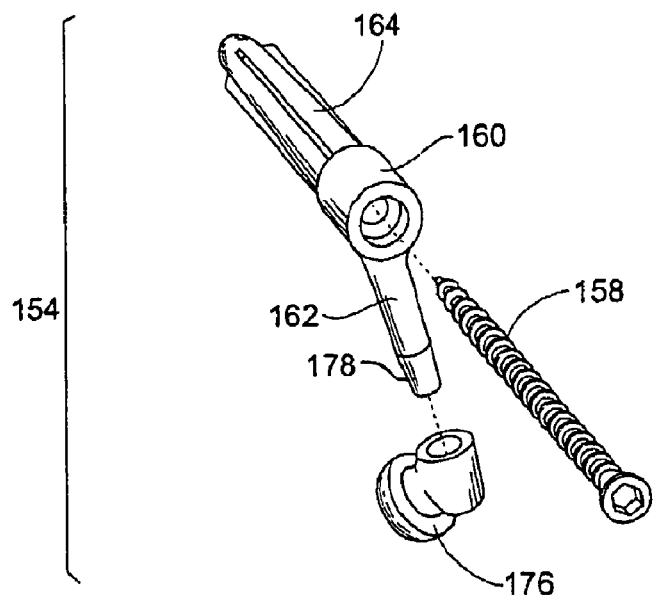
FIG. 26 is an alternative embodiment of the cephalad prosthesis shown in FIG. 24, illustrating the arm including a male fitting and the artificial facet joint structure including a female fitting.
Figure 27:
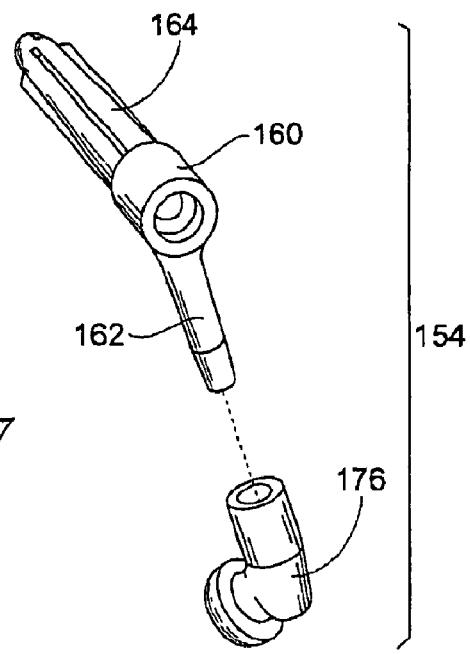
FIG. 27 is an alternative embodiment of the cephalad prosthesis shown in FIG. 26, and illustrating the artificial facet joint structure having a fitting elongated relative to FIG. 26.

FIG. 26 illustrates an alternative embodiment, in which the arm 162 includes a male fitting 178 and the artificial facet joint structure 176 includes a complementary female fitting 180. FIG. 27 illustrates how the fitting 178 may be extended to accommodate individual variations in anatomy. For example, the fitting 178 may be provided in a series of different lengths, e.g., 5, 6, 7, 8, 9 or 10 mm.

B. Caudal Prosthesis

Also similar to the previous embodiments, the caudal prosthesis 156 is a modular unit comprising a fixation element 184, a support 186, and an artificial facet joint structure 200 that allow assembly of the components in situ. A pair of fixation elements 184 (right and left) are desirably provided and sized and configured to be secured to the right and left pedicles 16 in an orientation that provides secure fixation to bone. Components are mounted in situ on the fixation elements 184 that are secured to the pedicle 16 in an orientation that provides secure fixation to bone.

In the illustrated embodiment, each fixation element 184 takes the form of a sleeve 190 and a pedicle screw 192, similar to the cephalad prosthesis 154. The sleeve 190 is sized and configured for placement within a bore 168 reamed in bone and can be secured by adhesive or by boney in-growth, as previously described. The sleeve 190 provides an increased surface area of attachment, further securing the attachment of the prosthesis 156 to bone. Desirably, the sleeve 190 includes a plurality of vanes 170 that resist rotation of the sleeve 190 in bone to further secure the sleeve 190 within the vertebra 12, as also previously described.

Figure 28:
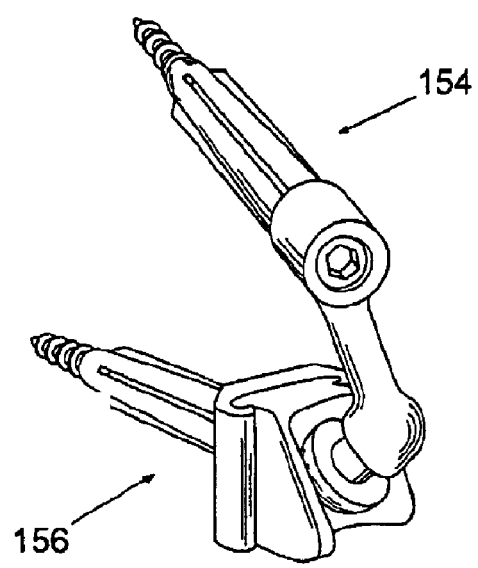
FIG. 28 is an assembled perspective view of the cephalad and caudal prostheses shown in FIG. 24.

A support 186 is integrally formed with the sleeve 190 or otherwise securely mounted on the sleeve 190. An opening 194 in the sleeve 190 extends through the support 186 and serves to receive the pedicle screw 192, e.g., by screwing the pedicle screw 192 into the sleeve 190. The support 186 is adapted to couple with the artificial facet joint structure 200. For example, in the illustrated embodiment, the support 186 carries a lip 196 which mates with a complementary lip 198 on the structure 200 to couple the structure with the support 186. The artificial facet joint structure 200 is sized and configured to articulate with the natural inferior facet portion of the facet joint 32 or an artificial facet joint structure 176 carried by the cephalad prosthesis 154 (FIG. 28).

C. Total Facet Replacement Using the Cephalad and Caudal Prostheses

In a surgical procedure for total facet replacement using the cephalad and caudal prostheses 154 and 156, some or all of the spinous process 22, along with the inferior articular process 28 and its supporting bone, of the upper half of the joint 32 (e.g., the cut inferior facet of the L4 vertebra in the L4-L5 joint) may be removed, as previously described (see FIG. 7). Prominent bone of the superior facet of the natural facet joint 32 (e.g., the superior articular process 26 and its supporting bone), may be also removed, as also previously described, using any means common in the field (see FIG. 7).

Figure 29:
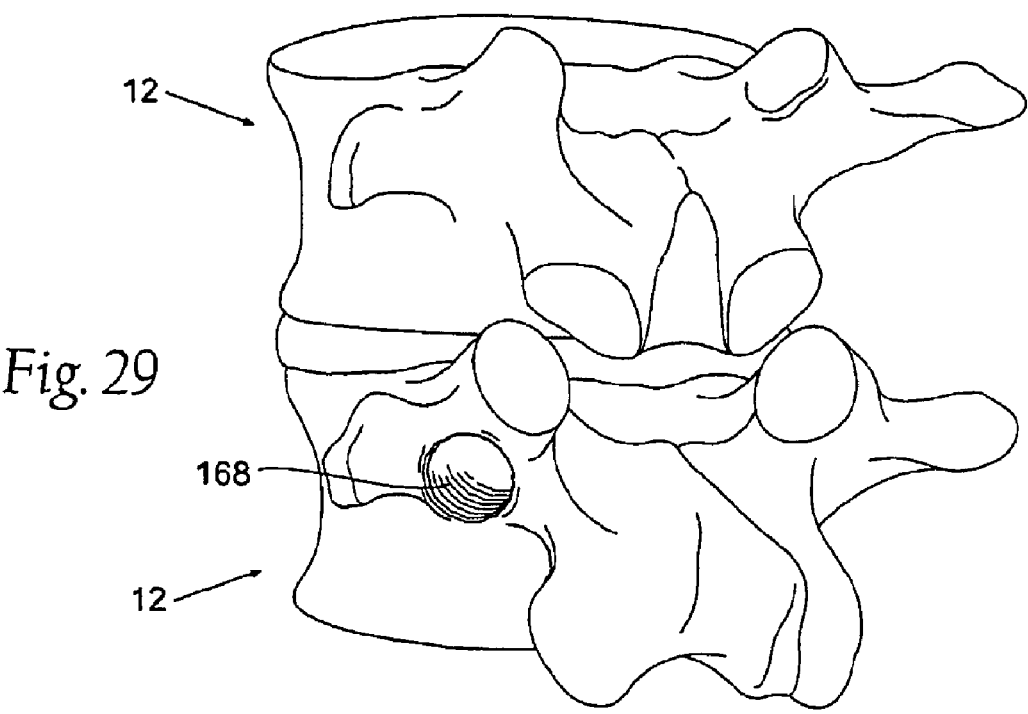
FIG. 29 is posterior perspective view of the lumbar vertebrae shown in FIG. 8, illustrating a bore reamed in a pedicle of the inferior vertebra.
Figure 30:
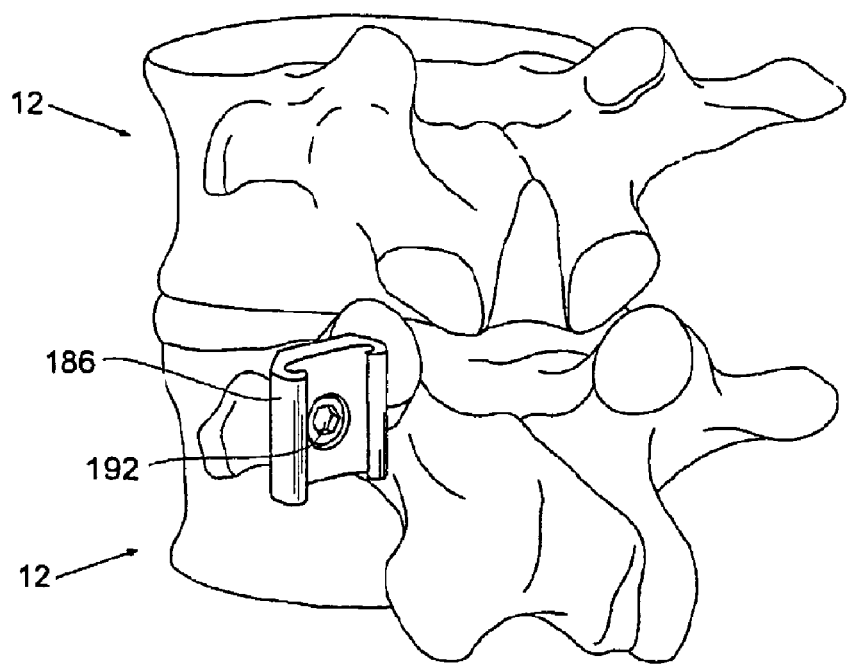
FIG. 30 is a posterior perspective view of the lumbar vertebrae shown in FIG. 29, illustrating the placement of a caudal sleeve, with a support mounted on the sleeve, within the bore.

As shown in FIG. 29, a bore 168 is reamed in a desired position in the pedicle 16 of the inferior vertebra 12 by conventional methods. If desired, mesh material 172 promoting boney in-growth is placed within the bore 168, as previously described (see FIG. 39). Alternatively, an adhesive material is placed within the bore 168 or along the outside of the caudal sleeve 190, as also previously described. The sleeve 190, with attached support 186, is then placed within the bore 168 and secured with a pedicle screw 192, as seen in FIG. 30.

Figure 31:
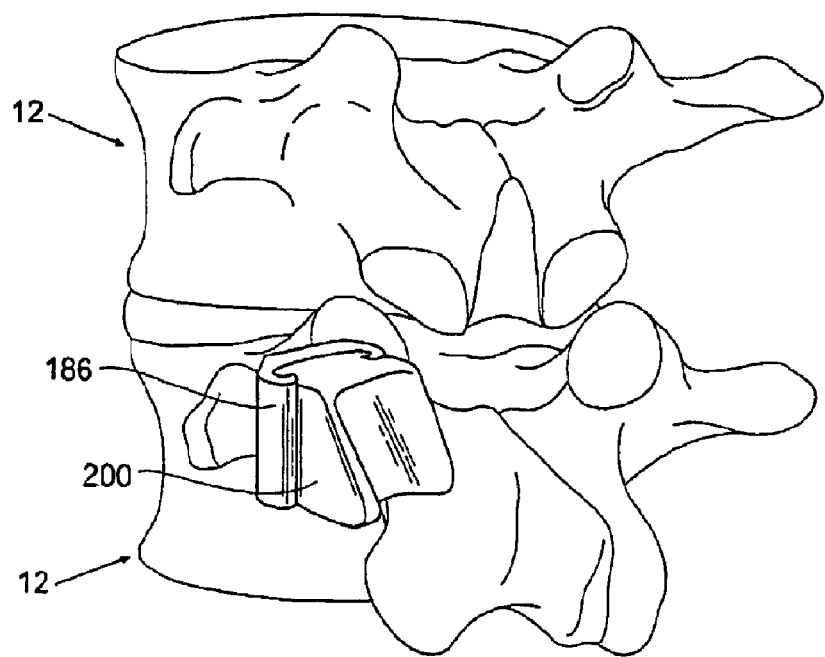
FIG. 31 is a posterior perspective view of the lumbar vertebrae shown in FIG. 30, illustrating the mounting of a caudal arm, carrying an artificial facet joint structure, on the caudal sleeve.

The caudal artificial facet joint structure 200, is then mounted on the caudal support 186, as shown in FIG. 31.

Figure 32:
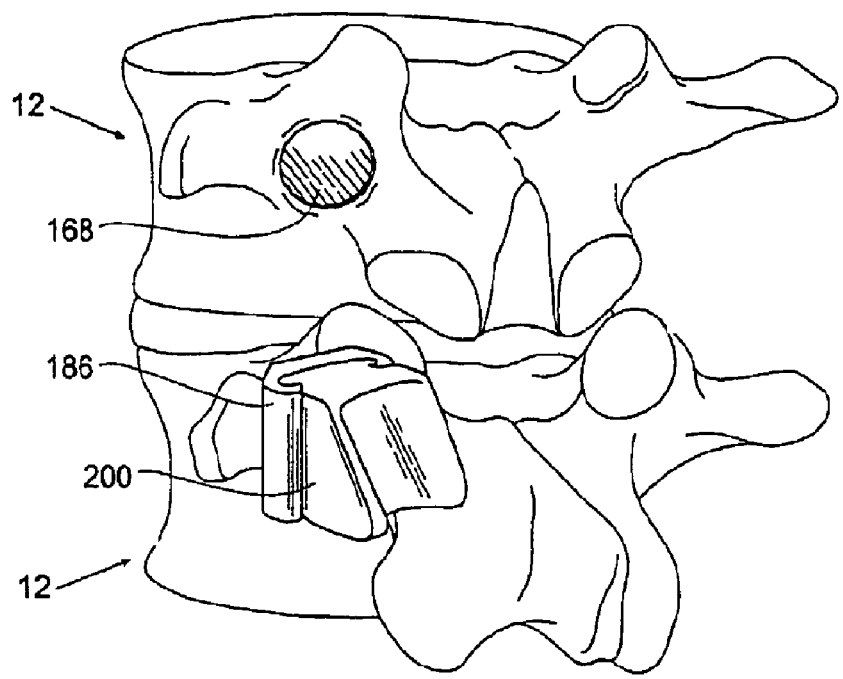
FIG. 32 is a posterior perspective view of the lumbar vertebrae shown in FIG. 31, illustrating a bore reamed in the complementary pedicle of the superior vertebra.
Figure 33:
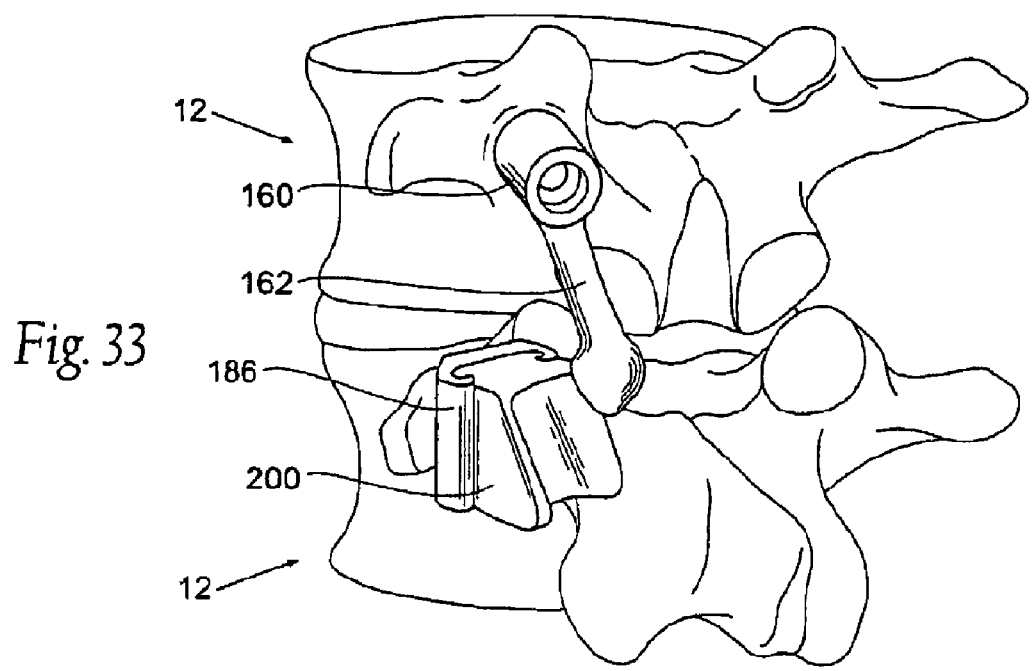
FIG. 33 is a posterior perspective view of the lumbar vertebrae shown in FIG. 32, illustrating the placement of a cephalad sleeve, with a support and arm mounted on the sleeve, within the bore.

As FIG. 32 illustrates, a bore 168 is reamed in a desired position in the corresponding pedicle 16 of the superior vertebra 12. The cephalad sleeve 164, with attached support 160 and arm 162 components, is placed within the bore 168 and secured by adhesive and/or boney in-growth mesh material 172, as shown in FIG. 39.

Figure 34:
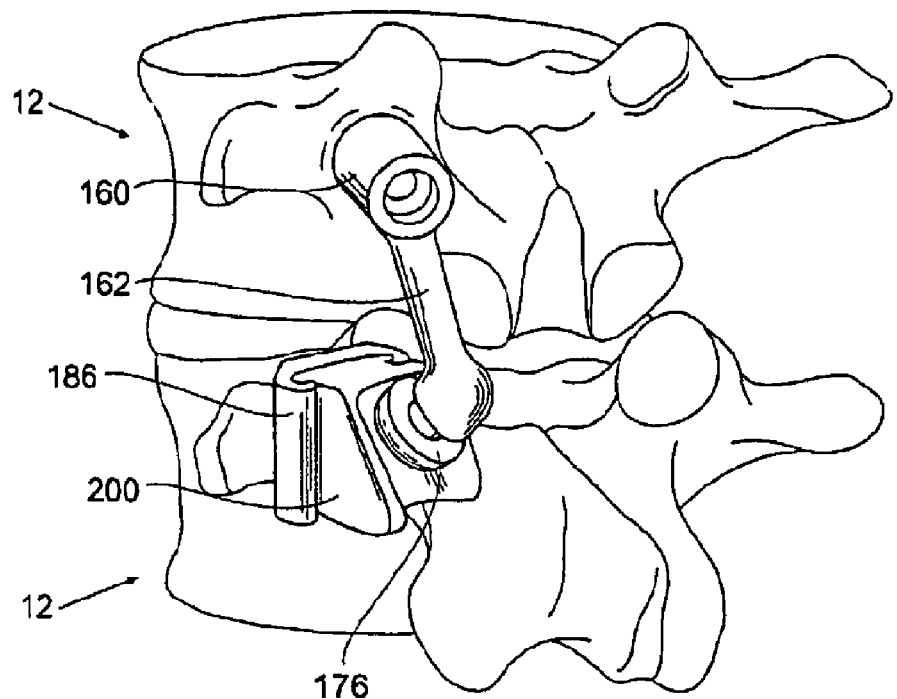
FIG. 34 is a posterior perspective view of the lumbar vertebrae shown in FIG. 33, illustrating the mounting on an artificial facet joint structure on the cephalad arm.
Figure 35:
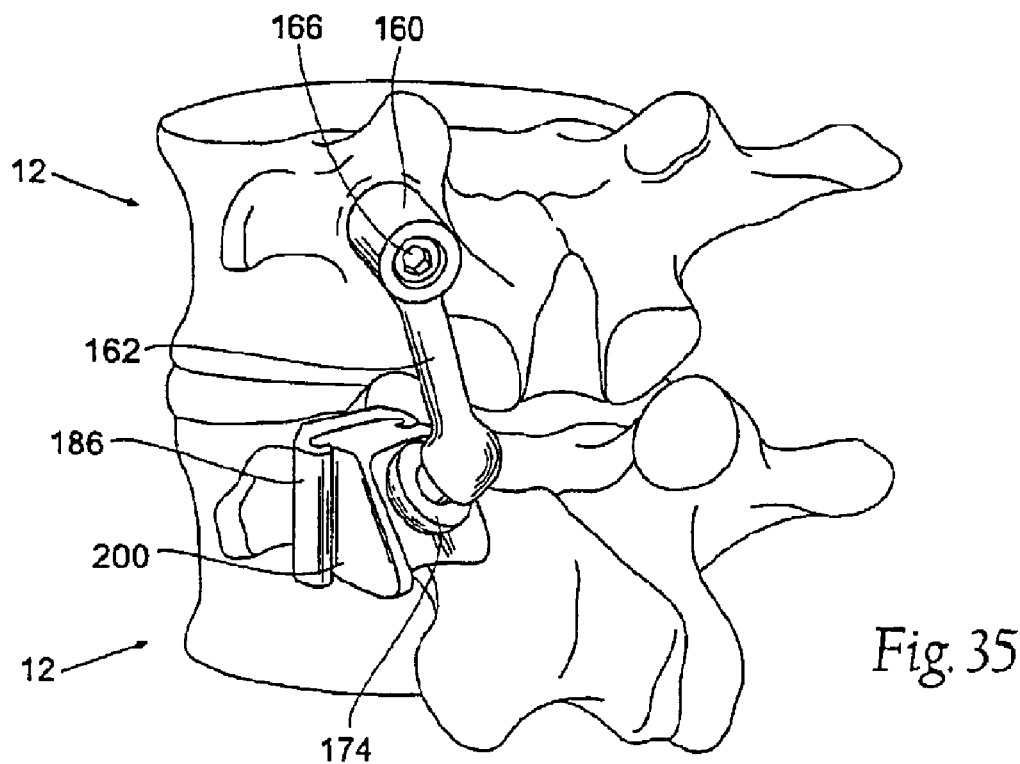
FIG. 35 is a posterior perspective view of the lumbar vertebrae shown in FIG. 34, illustrating the use of a pedicle screw to secure the mounting of the cephalad support and arm.

Next, with reference to FIG. 34, the cephalad artificial facet joint structure 176 is mounted on the cephalad arm 162. The position of the artificial facet structure 176 is then adjusted to assure articulation between artificial facet joint structures 200 and 176. The arm 162 is then secured in the desired position with a pedicle screw 166, as shown in FIG. 35.

Figure 36:
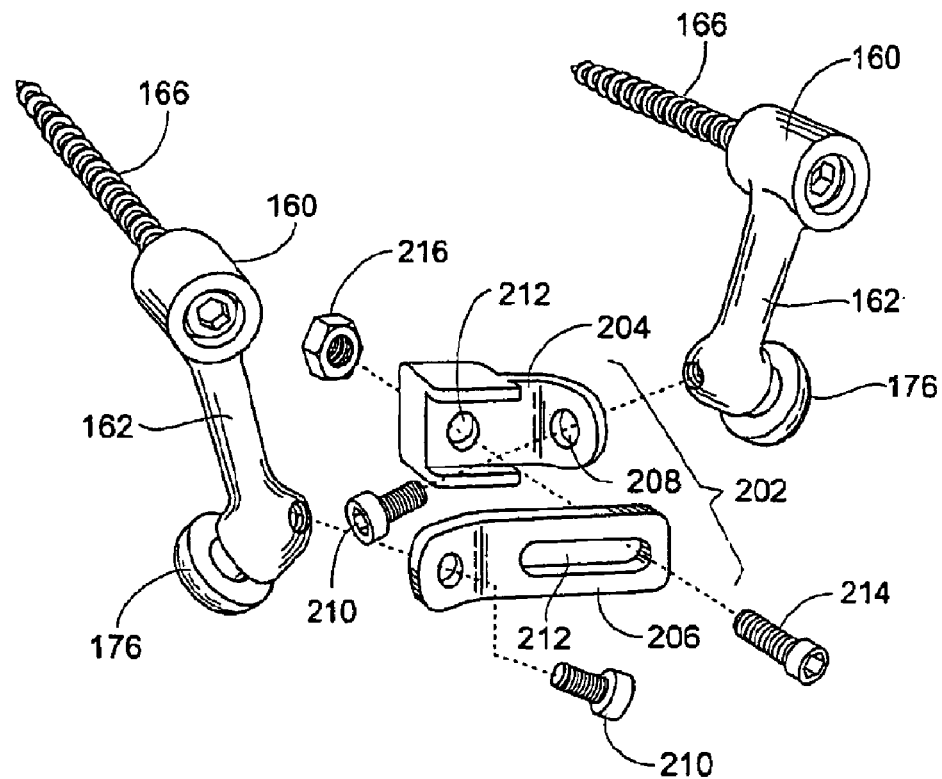
FIG. 36 is an exploded perspective view of a pair of cephalad prostheses joined by a transverse brace.

While FIGS. 29-35 illustrate unilateral facet joint replacement, it is often desirable to perform a bilateral facet joint replacement. In such an arrangement, as shown in FIG. 36, the left and right cephalad prostheses 154 may be coupled with a transverse brace 202. It is apparent that the brace 202 can be variously constructed. In the illustrated embodiment, brace 202 includes a right component 204 and a left component 206. An end opening 208 in each of the components 204 and 206 receives a fixation element 210 to fix the right and left components 204 and 206 to the right and left arms 162 respectively, e.g., by threaded engagement. Each component 204 and 206 desirably also has a medial opening 212. The medial openings 212 are sized and configured to overlap and permit passage of a fixation element 214, which may be secured by a nut 216 and bolt 214 or similar mechanism, to thereby couple the components 204 and 206 together to form the transverse brace 202. The brace 202 extends across the laminae 20 of a vertebral body 14, providing load-bearing support that further stabilizes the prostheses 154.

Figure 37:
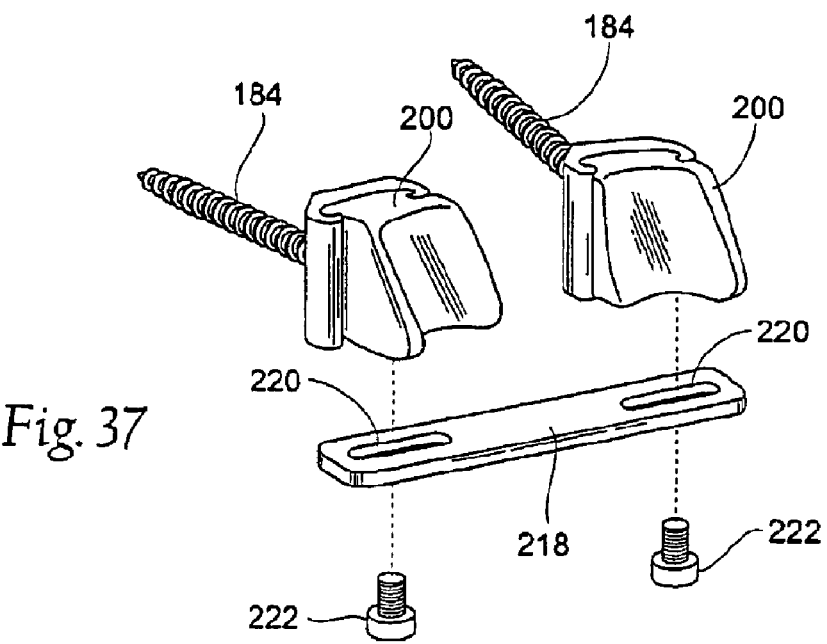
FIG. 37 is an exploded perspective view of a pair of caudal prostheses joined by a transverse brace.

Similarly, as seen in FIG. 37, the left and right caudal prostheses 156 may be coupled with a transverse brace 218. In the illustrated embodiment, the brace 218 takes the form of a transverse bar. The brace 218 includes a pair of end openings 220 (left and right) that permit passage of fixation elements 222 to secure the brace 218 to the left and right artificial facet joint structures 200, e.g., by threaded engagement. The braces 202 and 218 provide increased stability to the prostheses 154 and 156, as previously described.

Figure 38:
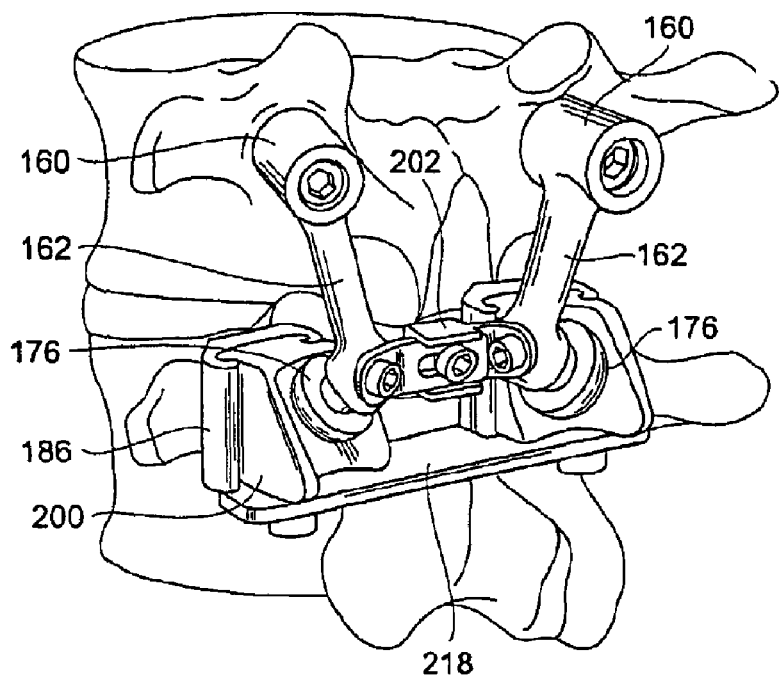
FIG. 38 is a posterior perspective view of the lumbar vertebrae shown in FIG. 35, illustrating bilateral cephalad and caudal prostheses fixed on the vertebrae using a pair of braces.

In this arrangement, as shown in FIG. 38, left and right cephalad prostheses 154 are secured within the left and right pedicles 16, respectively, of the superior vertebra 12, as previously described. Left and right caudal prostheses 156 are secured within the left and right pedicles 16, respectively, of the inferior vertebra 12, as also previously described. The cephalad prosthesis 154 are then coupled with brace 202, and the caudal prostheses 156 are coupled with brace 218.

It should be understood that, while the embodiments disclosed herein generally describe the complete repair/replacement of a pair of natural facet joints, the teachings of the present invention could be equally applicable to the repair/replacement of a single facet joint, or even the repair/replacement of a single cephalad or caudal portion of a single facet joint, or any combination thereof.

V. Spinal Unit Replacement

In the case of the combination of a facet prosthesis with an artificial disc 13 (desirably creating a total joint replacement in one or more functional spinal units), one or more components of the facet replacement prosthesis can be implanted into the vertebral body, into the artificial disc, or into a combination of both.

In the case of the combination of a facet replacement prosthesis with an artificial disc (desirably creating a total joint replacement in one or more functional spinal units), one or more components of the facet replacement prosthesis can be implanted into the vertebral body, into the artificial disc, or into a combination or of both. One concern currently existing with artificial disc replacement devices is the potential or tendency for the disk replacement components to "slip" or migrate within (or partially or totally out of) the inter-disc space post-surgery, especially where these components migrate towards the spinal cord, exiting nerve roots, or major spinal vasculature. Where the facet replacement prosthesis attaches to, connects to, or contacts (in some manner) one or more portions of the artificial disc prosthesis, however, the facet replacement prosthesis may advantageously reduce or eliminate the opportunity for the artificial disc prosthesis to migrate from a desired position within the disk space. Desirably, the facet replacement prosthesis is well secured into one or both of the vertebral bodies of the functional spinal unit, thereby well anchoring the artificial disc prosthesis as well. In fact, where the artificial disc prosthesis and the facet joint replacement prosthesis are each secured to each of the vertebral bodies (i.e., the facet joint replacement prosthesis secured into the pedicles and/or lamina of the vertebral bodies, and the artificial disc replacement prosthesis secured into the upper and lower endplates of the vertebral bodies), the resulting spine joint replacement construct would be extremely well anchored and unlikely to migrate or loosen. However, even where a portion of the facet replacement prosthesis is simply in contact with an artificial disc replacement device (or possibly positioned between the artificial disc replacement and the spinal cord, and not actually connected to or in immediate contact with the disc replacement), the presence of the facet replacement components could be a barrier to artificial disc components migrating towards the spinal cord.

The facet joint replacement components could connect or attach to an artificial disc replacement prosthesis in various manners, including through the interior of one or more vertebral bodies, or around the anterior, lateral or posterior walls of the vertebral body (and into the inter-disc space), or some combination of both.

In the case of annular repair and/or implantation of an artificial disc nucleus, it may be desirable that the facet replacement prosthesis bear a disproportionately higher share of the spinal load, thereby shielding the repaired and/or damaged tissue during natural healing or to prevent further degeneration or unacceptable loading on the other portions of the spine.

The above described embodiments of this invention are merely descriptive of its principles and are not to be limited. The scope of this invention instead shall be determined from the scope of the following claims, including their equivalents.

What is claimed is:

1. A system for treating spinal pathologies including an intervertebral disc prosthesis in combination with a facet joint prosthesis comprising:
    a first support component adapted to span a portion of the vertebral body and a second support component adapted to span a portion of the vertebral body; and
    a first prosthetic caudal facet element adjustable relative to the first support component and adapted to replace a caudal portion of a natural facet joint and a second prosthetic caudal facet element adjustable relative to the second support component and adapted to replace a caudal portion of a natural facet joint,
    wherein the first support component can be adjusted relative to a brace independently of the second support component.

2. The system of claim 1 wherein the first support component and/or second support component is sized to span a portion of the vertebral body between a left lamina and a right lamina.

3. The system of claim 1 wherein the first support component and/or second support component is sized to span a portion of the vertebral body between a left pedicle and a right pedicle.

4. The system of claim 1 further comprising a kit comprising a plurality of support components having different lengths.

5. The system of claim 1 wherein the first support component and/or second support component is further adapted to have an adjustable width.

6. The system of claim 1 further comprising one fixation element adapted to secure both prosthetic caudal facet elements to the vertebral body.

7. The system of claim 1 further comprising a fixation element adapted to attach the prosthesis to the vertebral body, the prosthetic caudal facet elements being further adapted to be movable with respect to the fixation element and the first support component and/or second support component.

8. The system of claim 1 further comprising a fixation element adapted to attach the prosthesis to the vertebral body, the first support component and/or second support component being further adapted to be movable with respect to the fixation element and the prosthetic caudal facet elements.

9. The system of claim 1 wherein the first support component and/or second support component is a curvilinear transverse rod.

10. The system of claim 1 wherein the prosthetic caudal facet elements are positioned relative to the first support component and/or second support component to provide a symmetric anatomical solution.

11. The system of claim 1 wherein the prosthetic caudal facet elements are positioned relative to the first support component and/or second support component to provide an asymmetric anatomical solution.

12. The system of claim 1 wherein the first support component and/or second support component has an opening to receive the caudal prosthesis elements.

13. The system of claim 12 wherein the prosthetic caudal facet elements are placed in the opening.

14. The system of claim 12 wherein the prosthetic caudal facet elements are adapted to be connected to the first support component and/or second support component with a fixation element placed through the opening.

15. The system of claim 14 wherein the prosthetic caudal facet elements are adapted to be connected to the first support component and/or second support component after the pair of caudal elements are secured to the vertebral body.

16. A surgical kit for treating spinal pathologies including an intervertebral disc prosthesis in combination with a facet joint prosthesis comprising:
    a first support component adapted to span a portion of the vertebral body and a second support component adapted to span a portion of the vertebral body; and
    a first prosthetic caudal facet element adjustable relative to the first support component and adapted to replace a caudal portion of a natural facet joint and a second prosthetic caudal facet element adjustable relative to the second support component and adapted to replace a caudal portion of a natural facet joint,
    wherein the first support component can be adjusted relative to a brace independently of the second support component.

17. The surgical kit of claim 16 wherein the first support component and/or second support component is sized to span a portion of the vertebral body between a left lamina and a right lamina.

18. The surgical kit of claim 16 wherein the first support component and/or second support component is sized to span a portion of the vertebral body between a left pedicle and a right pedicle.

19. The surgical kit of claim 16 further wherein the first support component and/or second support component is selected from a plurality of support components having different lengths.

20. The surgical kit of claim 16 wherein the first support component and/or second support component is further adapted to have an adjustable width.

21. The surgical kit of claim 16 further comprising one fixation element adapted to secure both prosthetic caudal facet elements to the vertebral body.

22. The surgical kit of claim 16 further comprising a fixation element adapted to attach the prosthesis to the vertebral body, the prosthetic caudal facet elements being further adapted to be movable with respect to the fixation element and the first support component and/or second support component.

23. The surgical kit of claim 16 further comprising a fixation element adapted to attach the prosthesis to the vertebral body, the first support component and/or second support component being further adapted to be movable with respect to the fixation element and the prosthetic caudal facet elements.

24. The surgical kit of claim 16 wherein the first support component and/or second support component is a curvilinear transverse rod.

25. The surgical kit of claim 16 wherein the prosthetic caudal facet elements are positioned relative to the first support component and/or second support component to provide a symmetric anatomical solution.

26. The surgical kit of claim 16 wherein the prosthetic caudal facet elements are positioned relative to the first support component and/or second support component to provide an asymmetric anatomical solution.

27. The surgical kit of claim 16 wherein the first support component and/or second support component has an opening to receive the caudal prosthesis elements.

28. The surgical kit of claim 27 wherein the prosthetic caudal facet elements are placed in the opening.

29. The surgical kit of claim 27 wherein the prosthetic caudal facet elements are adapted to be connected to the first support component and/or second support component with a fixation element placed through the opening.

30. The surgical kit of claim 29 wherein the prosthetic caudal facet elements are adapted to be connected to the first support component and/or second support component after the pair of caudal elements are secured to the vertebral body.

* * * * *